United States Patent
Barton et al.

(10) Patent No.: US 12,268,443 B2
(45) Date of Patent: Apr. 8, 2025

(54) THERAPEUTIC LASER SYSTEM AND METHOD OF USE FOR ACTIVATING THE TISSUE STEM CELL NICHE FOR THE TREATMENT OF MEDICAL CONDITIONS

(71) Applicant: KAIROS LASERS LLC, Osprey, FL (US)

(72) Inventors: Pamela Joy Barton, Osprey, FL (US); Bruno Gerald Frenguelli, Kenilworth (GB); Frank Joseph Rauscher, III, Wayne, PA (US)

(73) Assignee: KAIROS LASERS LLC, Osprey, FL (US)

( * ) Notice: Subject to any disclaimer, the term of this patent is extended or adjusted under 35 U.S.C. 154(b) by 0 days.

(21) Appl. No.: 18/376,322

(22) Filed: Oct. 3, 2023

(65) Prior Publication Data

US 2024/0108407 A1 Apr. 4, 2024

Related U.S. Application Data

(60) Provisional application No. 63/412,726, filed on Oct. 3, 2022.

(51) Int. Cl.
*A61N 5/06* (2006.01)
*A61B 18/20* (2006.01)
(Continued)

(52) U.S. Cl.
CPC ............ *A61B 18/203* (2013.01); *A61B 18/22* (2013.01); *A61B 2018/00327* (2013.01);
(Continued)

(58) Field of Classification Search
None
See application file for complete search history.

(56) References Cited

U.S. PATENT DOCUMENTS

| | | | |
|---|---|---|---|
| 5,445,146 | A | 8/1995 | Bellinger |
| 5,527,350 | A | 6/1996 | Grove et al. |

(Continued)

FOREIGN PATENT DOCUMENTS

| | | |
|---|---|---|
| DE | 69827286 T2 | 11/2005 |
| EP | 1021223 B1 | 7/2000 |

(Continued)

OTHER PUBLICATIONS

International Search Report and Written Opinion regarding PCT/US23/34394, dated Feb. 7, 2024, 11 pages.

*Primary Examiner* — Lynsey C Eiseman
(74) *Attorney, Agent, or Firm* — Richard Kosakowski

(57) ABSTRACT

A system for treating various medical conditions in humans includes a medical or therapeutic laser operating at wavelengths in the near infrared range of between 1250 nm-1267 nm, with a target wavelength of 1260 nm, at power levels between 2 Watts and 60 Watts, and for a period not to exceed 60 seconds per dose. The emitted laser light energizes, e.g., the stem cell niche or mitochondria of the human tissue to which it is applied, both directly and indirectly via activation of cell signaling intermediaries including but not limited to heat shock proteins, thereby stimulating cell activity to promote healing and reduce pain. In this specific wavelength range, water absorption of the laser light energy is plateaued which effectively acts as a conduit allowing the laser light energy to be transferred deeper into the tissue without causing thermal damage to the skin and tissue.

2 Claims, 18 Drawing Sheets

(51) Int. Cl.
*A61B 18/22* (2006.01)
*A61B 18/00* (2006.01)

(52) U.S. Cl.
CPC ............... *A61B 2018/00458* (2013.01); *A61B 2018/0047* (2013.01); *A61B 2018/00565* (2013.01); *A61B 2018/00702* (2013.01); *A61B 2018/00714* (2013.01); *A61B 2560/02* (2013.01)

(56) References Cited

U.S. PATENT DOCUMENTS

| | | | |
|---|---|---|---|
| 5,951,596 | A | 9/1999 | Bellinger |
| 6,063,108 | A | 5/2000 | Salansky et al. |
| 7,730,893 | B2 | 6/2010 | Dougal |
| 8,968,221 | B2 | 3/2015 | Pryor et al. |
| 9,314,302 | B2 | 4/2016 | Dougal |
| 9,764,155 | B2 | 9/2017 | Pryor et al. |
| 10,238,889 | B2 | 3/2019 | Pryor et al. |
| 10,589,120 | B1* | 3/2020 | Bellinger ............. A61N 5/0613 |
| 10,965,091 | B2 | 3/2021 | Waterbury et al. |
| 2004/0093042 | A1* | 5/2004 | Altshuler ............. A61B 18/203 607/88 |
| 2005/0234383 | A1 | 10/2005 | Dougal |
| 2010/0049180 | A1* | 2/2010 | Wells ................... A61N 5/0616 606/11 |
| 2015/0182755 | A1 | 7/2015 | Bellinger |
| 2015/0265725 | A1* | 9/2015 | Peyman ............... A61B 5/0095 604/20 |
| 2016/0296764 | A1 | 10/2016 | Bellinger |
| 2017/0027642 | A1* | 2/2017 | Schuster ............. A61B 18/203 |
| 2017/0203132 | A1* | 7/2017 | Luttrull ............. A61B 18/1492 |
| 2019/0262072 | A1* | 8/2019 | Sakamoto ............ A61N 1/0484 |
| 2020/0163899 | A1 | 5/2020 | Fernandes et al. |
| 2020/0360724 | A1 | 11/2020 | Dunleavy et al. |
| 2021/0228412 | A1 | 7/2021 | de Juan et al. |

FOREIGN PATENT DOCUMENTS

| | | |
|---|---|---|
| WO | 9830283 A1 | 7/1998 |
| WO | 1999019024 A1 | 4/1999 |
| WO | 0035534 A1 | 6/2000 |
| WO | 2014110149 A2 | 7/2014 |
| WO | 2017004444 A1 | 1/2017 |

* cited by examiner

| Distance to Skin | Aim Beam Size | 1260 nm Beam Size | Diameter | Radius | Area | Laser Power Density (Irradience) W/cm2 | | | | | |
|---|---|---|---|---|---|---|---|---|---|---|---|
| | | | | | | 40 | 35 | 30 | 20 | 10 | 5 |
| 10" | 1.82"<br>4.625cm | 4.49"<br>11.41cm | 11.41 | 5.71 | 102.25 | 0.39 | 0.34 | 0.29 | 0.20 | 0.10 | 0.05 |
| 9" | 1.67"<br>4.25cm | 4.11"<br>10.46cm | 10.46 | 5.23 | 85.93 | 0.47 | 0.41 | 0.35 | 0.23 | 0.12 | 0.06 |
| 8" | 1.52"<br>3.875cm | 3.74"<br>9.51cm | 9.51 | 4.76 | 71.03 | 0.56 | 0.49 | 0.42 | 0.28 | 0.14 | 0.07 |
| 7" | 1.37"<br>3.5cm | 3.37"<br>8.56cm | 8.56 | 4.28 | 57.55 | 0.70 | 0.61 | 0.52 | 0.35 | 0.17 | 0.09 |
| 6" | 1.23"<br>3.125cm | 2.99"<br>7.61cm | 7.61 | 3.81 | 45.48 | 0.88 | 0.77 | 0.66 | 0.44 | 0.22 | 0.11 |
| 5" | 1.08"<br>2.75cm | 2.75"<br>6.67cm | 6.67 | 3.34 | 34.94 | 1.14 | 1.00 | 0.86 | 0.57 | 0.29 | 0.14 |
| 4" | .93"<br>2.375cm | 2.25"<br>5.715cm | 5.72 | 2.86 | 25.70 | 1.56 | 1.36 | 1.17 | 0.78 | 0.39 | 0.19 |
| 3" | .787"/2cm | 1.875"<br>4.76cm | 4.76 | 2.38 | 17.80 | 2.25 | 1.97 | 1.69 | 1.12 | 0.56 | 0.28 |
| 2" | .63"<br>1.625cm | 1.5"<br>3.81cm | 3.81 | 1.91 | 11.40 | 3.51 | 3.07 | 2.63 | 1.75 | 0.88 | 0.44 |
| 1" | .49"<br>1.25cm | 1.12"<br>2.86cm | 2.88 | 1.44 | 6.51 | 6.14 | 5.37 | 4.61 | 3.07 | 1.54 | 0.77 |

FIG. 19

THERAPEUTIC LASER SYSTEM AND METHOD OF USE FOR ACTIVATING THE TISSUE STEM CELL NICHE FOR THE TREATMENT OF MEDICAL CONDITIONS

CROSS-REFERENCE TO RELATED APPLICATIONS

The present application claims the benefit of U.S. Provisional Patent Application No. 63/412,726, filed Oct. 3, 2022, the contents of which are incorporated by reference herein.

FIELD OF THE INVENTION

The subject matter disclosed herein relates in general to therapeutic lasers, and more specifically to a therapeutic laser system used to treat a wide range of medical conditions and having a laser that emits light at a specific wavelength and where the laser light is delivered with specific energy parameters within the near infrared (IR) spectrum, which is defined generally as wavelengths between 700 nanometers (nm) and 2500 nm, to optimize the depth of penetration of the laser light into human tissue and minimize non-target absorption (scatter) of the laser light within the body.

BACKGROUND OF THE INVENTION

Known, prior art laser-based systems and devices for treatment of various medical conditions typically include a therapeutic or medical laser and means for controlling various parameters related to the application of the laser light beam to specific parts of the body. These parameters include the wavelength of the laser light along with the power level and duration time of the application of the laser light—i.e., the dosage or Joules of energy delivered of the applied laser light (irradiance). The laser light energy is claimed to interact with the body cells and tissue to stimulate the regeneration and healing of the cells and tissue and to decrease the amount of pain. This light energy and tissue interaction is typically referred to as photobiomodulation (PBM).

In general, the wavelength of the laser light determines the thermal effect of that light as it travels through the layers of the skin and into the underlying tissues. The thermal effect ultimately limits the ability of the laser to be used to deliver higher doses of energy or to access deeper levels of tissue, or to deliver energy in a targeted fashion without scatter into peripheral non-target tissues. It is known that therapeutic or medical lasers having wavelengths in the IR or near IR regions of the overall light spectrum are used. Laser light having IR wavelengths are longer in wavelength than light in the visible spectrum. These IR wavelengths of light can in some circumstances penetrate deeper into tissue than do light of shorter wavelengths. In general, longer wavelengths are associated with tissue heating. Lasers within the IR spectrum (e.g., 1300 nm) are typically used in medical practice for e.g., tissue cutting because of their thermal effects in tissue.

As the wavelength of the laser is increased, the likelihood of the laser light causing burning of the skin also increases. As such, prior art laser systems and devices often incorporate cooling heads in an attempt to mitigate any burning of the skin. For example, lasers of wavelength 1064 nm are widely known and typically used with skin cooling modalities. Yet, the use of cooling heads adds to the complexity and cost of the overall system. A type of laser known as cold lasers emit light energy that is absorbed into the body without heating the body. Many of these cold lasers are typically operated at wavelengths below 1200 nm and at relatively low power levels in the range of microwatts or milliwatts. For example, an aiming beam that is a cold laser emitting milliwatts of energy at the 650 nm wavelength is of zero therapeutic utility.

It would be beneficial to utilize lasers for therapeutic or medical purposes where the lasers are operated at longer wavelengths in the range of between 1250 nm-1267 nm, with a target wavelength of 1260 nm, and at higher power levels between 2 Watts and 60 Watts depending upon the tissue type to be treated. This would allow for relatively deeper penetration of the laser light through the skin and/or bone and into soft tissues without causing thermal damage to the tissue types that the laser light passes through.

Therefore, what is needed is a system that incorporates a laser and a method for operating the laser at a certain combination of wavelength, power level, and duration time to safely and consistently effectively treat a wide range of medical conditions that include both injuries to and diseases of the body in humans.

BRIEF SUMMARY OF THE INVENTION

An object of embodiments of the present invention is to provide a laser-based system and method of use which rapidly and non-invasively, and in a reliable and consistent fashion, treats and restores injured tissues of a body, thereby immediately reducing inflammation and pain while speeding up the healing of damage to allow individuals to recover faster and better.

Another object of embodiments of the present invention is to provide a non-invasive, drug-free, laser-based system and method of use which accelerates the healing process, thereby quickly restoring body function and/or physical movement and thus, confidence and quality of life.

Yet another object of embodiments of the present invention is to provide a laser-based system and method of use which reduces inflammation and relieves both acute and chronic pain in the body to stimulate the healing process in the body, thereby allowing the person to regain their range of physical motion and mobility and return to normal functioning in a shorter time period.

Still another object of embodiments of the present invention is to provide a laser-based system and method of use which can be utilized by a wide range of medical professionals such as orthopedists, pain specialists, chiropractors, and general practitioners to treat their patients.

Another object of embodiments of the present invention is to provide a laser-based system and method of use which can be utilized by a wide range of people such as professional athletes, professional and collegiate sports teams, as well as weekend sportspersons and everyday people who are experiencing various injuries and diseases.

Yet another object of embodiments of the present invention is to eliminate the use of cooling heads or any other type of cooling devices in conjunction with the operation of a laser device that is part of a laser-based system for treatment of various medical conditions such as, for example, sports injuries, sports conditioning, wound healing, peripheral paresthesia including diabetic, fibrosis, shingles, neuralgia, and many others.

Still another object of embodiment of the present invention is to provide a laser-based system and method of use in which a consequence of the selected wavelength and power combination for operation of the laser has a specific profile of chromophore activation that does not heat up the skin and other non-target tissues to the same degree as other wavelength and power combinations.

Yet another object of embodiments of the present invention is to provide a laser-based system and method of use which utilizes a therapeutic laser to deliver doses of energy with significantly less non-target tissue scatter, absorption, and heating within the body, allowing for a higher level or dose of energy to be delivered to the stem cell niche (SCN) without causing excessive heating or thermal damage to non-target tissues (e.g., skin).

Another object of embodiments of the present invention is to provide a laser-based system along with specific methods of use or protocols for treatment of varying medical conditions, and where the protocols vary primarily in their applied laser light power levels (i.e., irradiance).

According to exemplary embodiments of the present invention, a system for treating various medical conditions in humans includes a medical or therapeutic laser operating at wavelengths in the near infrared range of between 1250 nm-1267 nm, with a target wavelength of 1260 nm, at power levels between 2 Watts and 60 Watts, and for a time period not to exceed 60 seconds per dose. The emitted laser light at this combination of wavelength, power level, and duration is such that it, e.g., energizes the stem cell niche or mitochondria of the human tissue to which it is applied, both directly and indirectly via activation of cell signaling intermediaries including but not limited to heat shock proteins, thereby stimulating cell activity to promote healing and reduce pain. In this specific wavelength range, water absorption of the laser light energy is plateaued which effectively acts as a conduit allowing the laser light energy to be transferred deeper into the tissue without causing thermal damage to the skin and tissue.

BRIEF DESCRIPTION OF THE DRAWINGS

The foregoing and other features and advantages of the present invention will become more apparent from the following detailed description taken in conjunction with the accompanying drawings in which:

FIG. 19 is a table showing the resulting power density of the laser of the laser-based system of FIG. 1 with other system parameters being varied, according to exemplary embodiments of the present invention;

DETAILED DESCRIPTION OF THE INVENTION

Figure 1:
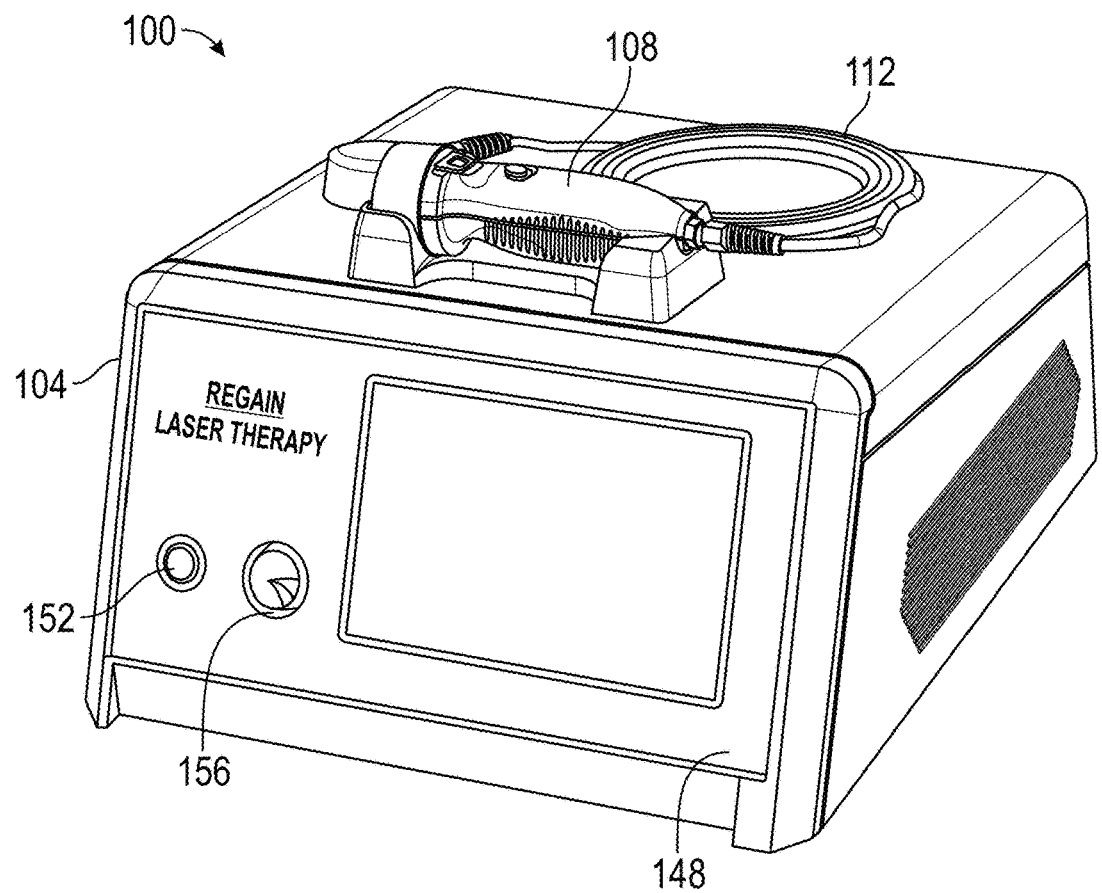
FIG. 1 is a perspective view of a laser-based system for treating various medical conditions, according to an exemplary embodiment of the present invention.

Described and illustrated in detail herein are various exemplary embodiments of the present invention of a laser-based system 100 (FIG. 1) and associated methods of use for treatment of various medical conditions in humans. These embodiments include and utilize a therapeutic or medical laser that operates at a specific combination of: (1) a wavelength in the near IR region of the spectrum (e.g., in a wavelength range between 1250 nm-1267 nm, and at a particular wavelength of 1260 nm); (2) a power level (e.g., 2 Watts to 60 Watts); and (3) a duration time (e.g., no greater than 60 seconds). The power level or irradiance and duration time of the applied laser light combine to form the dose of the laser (i.e., the number of Joules of energy delivered), which controls the laser light to safely and effectively treat a wide range of medical conditions that include both injuries to and diseases of the body.

The present inventors have discovered that there is a plateau in water absorption of laser light at wavelengths in the near IR range of approximately 1250 nm-1267 nm. Below a wavelength of 1250 nm, there is not enough energy in the applied laser light, and thus there is an inconsistent effect if any in tissue treatment effectiveness. That is, below 1250 nm the laser light energy is absorbed by and scattered into non-target peripheral tissues, which causes a large amount of non-target tissue heating and potential burning. This limits the ability of the laser to access its target and limits the amount of energy that can be delivered.

On the other hand, above a wavelength of 1300 nm, there is excess energy in the applied laser light and burning of the skin may occur. Thus, there exists a laser wavelength plateau having a bandwidth of approximately 50 nm where laser light can be effectively directed into body tissue to restore the tissue. That is, the water absorption plateau can be utilized to overcome the energy threshold without burning of the skin. This is true for all Fitzpatrick skin types.

More specifically, it has been discovered that at laser wavelengths in the range of 1250 nm-1267 nm (plus or minus 20 nm, which is the current approximate tolerance band of diode lasers), the combined absorption by melanin and haem of the laser light energy is low enough to allow the energy applied in the range of 2 Watts to 60 Watts for up to 60 seconds (i.e., spot treatment) to pass through skin without burning. A specific wavelength of 1260 nm has been found to be most effective. The power setting of the laser may be adjusted within the range of 2 Watts to 60 Watts depending upon both the depth of penetration and the power density of the laser light necessary to access or activate the stem cell niche (SCN), the intracellular and extracellular matrices, and the phospholipid layers of the target tissue.

Depending upon how close the laser diode is to the skin, the same power density can be achieved in the range of 2 Watts-60 Watts. However, the same field size cannot be achieved. For areas such as the sinuses, a relatively tight or small field size is preferred; thus, the power is reduced and the laser is located relatively close to the skin. For larger areas such as the lower back, it is beneficial to apply the laser light at a higher power level with a wider field size and for a shorter amount of time.

In the same specific wavelength range of 1250 nm-1267 nm (and more specifically and particularly at 1260 nm), water absorption is plateaued which effectively acts as a conduit allowing for laser light energy to be transferred deeper into the tissue without heating to the point of burning. This allows for a threshold effect in which the energy overcomes a threshold level and elicits an effect within the SCN of the target tissue that promotes signaling to facilitate remodeling of tissues. This is a thermal effect in non-inflamed tissues. The energy promotes a more dynamic phospholipid environment allowing energy penetration into the tissue without heating of the tissue while also changing phospholipid and intracellular and extracellular signaling to cause remodeling of and modifications in the tissues. The same effect can be achieved using continuous wave or pulsed wave lasers at these wavelengths and power settings.

In stable scars, stable fibrous tissue, and wounds—especially but not limited to the central nervous system (CNS)—the laser stimulates both interstitial collagenases and Yamanaka Factor (YF) stimulation, which leads to stem cell maturation and remodeling of the tissues. A SCN is an area of a tissue that provides a specific microenvironment in which stem cells are present in an undifferentiated and self-renewable state. Cells of the SCN interact with the stem cells to maintain them or promote their differentiation. The water absorption plateau allows for a greater amount of energy to be applied (i.e., a threshold level of energy that must be overcome) and once that threshold has been overcome, the combination of collagenases destroying scar tissue and stem cell maturation leads to remodeling to the correct tissue type.

In brain tissue, the energy transfer is preferentially absorbed by the chromophores elastin and fibrin resulting in remodeling of glial and other scars via normal tissue healing mechanisms such as angiogenesis, macrophage migration, IFN, etc. This remodeling of the scar tissue, uniquely possible because of the deeper tissue penetration and water conduit effect, promotes the remodeling of CNS lesions typical of e.g., TBI, Parkinson's, Alzheimer's, mixed dementias, etc. This is a thermal effect in non-inflamed tissues. The same effect can be achieved using continuous wave or pulsed wave lasers at these wavelengths. The key parameter is the thermal effect at depth where "thermal" describes the delivery of photons of energy to the mitochondria and creating an energy gradient at depth.

The methods described and illustrated in detail herein include a method of treating pathological fibrous tissue deposition and/or damaged tissue that is in the process of healing. This treatment is done to rapidly remodel the tissue, whereby the treatment to remodel the tissue is delivered by a laser. A laser operating at 1260 nm and within an applied power range of 2 Watts-60 Watts is uniquely able to penetrate tissue and cause in vivo mechanistic changes that induce repair in stable (non-inflamed) tissue, damaged tissue, and/or dysfunctional mammalian tissues (e.g., frozen shoulder, Dupuytren's contracture, plantar fasciitis, and others) without causing thermal damage. When employing this method, the mechanism of repair may include, for example, activation of the SCN, which provides for more robust reliable and consistent results than previously described prior art methodologies.

The method of treatment disclosed herein is unique in that it exploits a wavelength range which is specifically selected because it has the optimal and unique combination of minimal absorption of light energy by haem and oxyhemoglobin, minimal absorption of light energy by melanin, and non-linear absorption of light by water. That is, there is lower water absorption than we would anticipate if there were a fully linear relationship in the specific area of the wavelength range of 1250 nm-1267 nm. The method also exploits a power setting that allows the laser energy to be directed from between 1 cm to up to 30 cm into the body depending upon the target area to be activated. These factors uniquely combine to allow higher levels of light energy (i.e., a higher dose) to be delivered into target (damaged) tissues, especially into the SCNs of the target tissues, than can be obtained with other combined wavelength/power approaches and without thermal damage to the tissues. The doses of energy contemplated herein are delivered with significantly less non-target tissue scatter and heating, allowing for a higher level or dose of energy to be delivered to the SCN without causing excessive heating or thermal damage to non-target tissues (e.g., skin).

Thus, embodiments of the present invention can uniquely without burning and uniquely without the need for skin cooling, deliver enough energy to create an energy gradient in the SCN with the net result of energetic activation of the SCN. This energetic activation is manifest as the activation of dormant stem cell progenitors, and the differentiation of progenitor stem cells into effector cell types, accompanied with the release of cytokines associated with tissue repair, inhibition of cytokines associated with the promotion of dysfunctional healing (e.g., scar formation), and an upregulation of genes associated with enhanced metabolism and successful healing. The envisaged laser therapy is further suitable for use in all skin including tanned skin due to its minimal absorption by melanin, and for use without the need for shaving e.g., companion animals (cats and dogs), horses, and camels.

While the SCN itself is historically an elusive tissue area and is different within each tissue type, a secondary marker for SCN activation is an increase in skin temperature at the area of the skin that the laser is applied. This skin temperature increase is a surrogate marker for internal energy level changes within the SCN. For the treatment contemplated herein to be effective, during a treatment session the skin temperature must increase but by no more than 10 degrees Celsius (° C.), and this delta should be maintained at +10° C. for at least 45 seconds. This skin temperature increase is a surrogate marker for internal energy changes. In the absence of the delivery of an adequate dose of energy, activation of the SCN does not occur. Thus, the present inventors postulate that there is a threshold energy level required to be overcome in order for the SCN to be activated, and that this threshold is uniquely overcome by the combination of wavelength, power settings, and duration contemplated herein.

Further, there are multiple SCNs, skin, muscle, brain, etc. to be considered. Thus, to effect correct healing at the appropriate tissue level, the power settings of the laser must be adjusted to access, for example, a skin SCN that is relatively shallow, or a muscle SCN that is somewhat deeper. The ability to penetrate bone also allows for the mobilization of stem cell mediated remodeling of soft tissue of neural origin e.g., brain. Thus, the specific combination of wavelength and power of the laser light utilized is important. Increasing power but using wavelengths other than 1260 nm (e.g., 1230 nm or 1280 nm) would result in peripheral tissue heating and thermal damage. Thermal damage would occur before the SCN was activated, and this thermal damage would limit energy penetration. Also, power levels greater than 60 Watts at 1260 nm have been shown to cause thermal damage. Further, at power levels lower than 2 Watts, there is not sufficient energy for activation of the SCN (other than for activation of the basil lamina SCN), and the changes in cytokine and gene expression associated with SCN activation are not seen. The use of the laser can be further finetuned, when used combined with modalities to detect tissue densities—e.g., ultrasound, MRI, etc., to provide for a more precise determination of power delivery at the target site. There are instances where one would want to be more precise—for example, someone with a lot of skin and adipose on their skull is going to have a different power setting than someone with a relatively bony, skinny head. Where the precision is necessary, it is preferred to use a paired diagnostic approach to be able to determine the level of adipose to penetrate and alter the power settings accordingly.

Thus, both wavelength and power together combine to allow greater energy accessibility and generation into target tissue SCNs than can be obtained with other wavelength and power combinations. This delivery of a higher level of energy to the SCN results in the development of an energy gradient in the SCN which allows for Yamanaka factor activation and leads to the stimulation of tissue repair, such repair being SCN tissue type specific. Other wavelength and power combinations are unable to deliver as much energy directly to the SCN due primarily to their different melanin, haem, oxy haem, protein, fat, and water absorption profiles which lead to tissue heating and scatter of energy which in combination reduce the energy delivery to the SCN and prevent activation of the SCN. Also, other lasers at different wavelength and power combinations are not able to deliver enough energy to activate the SCN because, due to their absorption spectra, they cause excessive peripheral heating and thus, they cause thermal damage before they reach the SCN. The relatively small degree of peripheral tissue heating and activation that does occur with embodiments of the laser treatment method of the present invention results in significant vasodilation in the area of the SCN without causing thermal damage. That vasodilation effectively acts as an enhanced conduit for SCN activation and messenger protein expression and transport. Therefore, the wavelength and power combination allow the SCN to be activated to effect healing.

In general, when the wavelength of light approximates the size of the particles (i.e., biological components—e.g., collagen) that the light is traveling through, the light is pulled forward and is not deflected or scattered by the particles. This is known as the Mie effect. When near IR light in the wavelength range of 1250 nm-1267 nm is radiated onto skin for travel into the skin (i.e., the dermis and epidermis), the size of the particles in the skin (e.g., collagen fibrils, keratin molecules, etc.) is approximately the same size as the photons of light. Thus, within this particular wavelength range, the photons are largely neither scattered nor deflected, but continue in their direction of travel. The medium through which the light is traveling (e.g., melanin, hemoglobin, oxyhemoglobin, protein, fat) has relatively low ability to absorb the light and absorb its energy. Water is the most active chromophore and the molecule with the most absorptive capacity. Thus, the light energy gets pulled through the tissue due to the Mie effect with very little scatter or absorption until it reaches an area of relatively high-water content, which is the SCN. As such, with the laser of embodiments of the present invention operating within the wavelength range of 1250 nm-1267 nm and at varying power levels of 2 Watts to 60 Watts, there is very low or minimal amounts of undesirable laser light scatter into non-target tissues and thus, little to no off-target heating of tissue. That is, most of the laser light energy is focused onto the target tissue for optimal therapeutic healing effect. Thus, uniquely the wavelength band of 1250 nm-1267 nm is subject to Mie forward scatter—i.e., the tissue effectively pulls the energy forward through the tissue until the energy hits a chromophore—water most often to be found in the SCN.

Deflection of energy and absorption of energy by water, protein, hemoglobin, oxyhemoglobin, and melanin is minimal but not zero in the wavelength range of 1250 nm-1267 nm. The minimal deflection and absorption allow for a greater amount of energy to be delivered without tissue heating. Above 1300 nm, energy absorption by water increases almost exponentially and this results in tissue heating to a level that is of no therapeutic utility.

The first high-water tissue or high-water containing tissue area below the dermis is the SCN in the basal lamina. This SCN is an area of relatively high-water content due to the composition of its specialized extracellular matrix. Specifically due to the water content, this area acts as a chromophore absorbing energy. The absorbed energy stimulates cellular activity and creates an energy gradient effectively resulting in a high energy activated SCN. The small amount of energy absorbed by water, protein, hemoglobin, oxyhemoglobin, and melanin as the energy passes through the tissue results in vasodilation setting up a positive feedback loop to allow SCN activation.

For consistent effects, the energy applied must be high enough to activate the SCN but not so high as to burn the skin. There is considerable heterogeneity in human skin and even more heterogeneity when human skin and animal skin are compared. There are different levels of melanin at different depths as well as different fat content, different protein (muscle) content, and even different degrees of oxygenated and deoxygenated hemoglobin as a consequence of circulatory deficits such as Raynaud's syndrome and diabetes.

The present inventors have discovered that in utilizing skin temperature as a secondary marker, and by application of near IR light energy using a handpiece with a Gaussian distribution of light in a pattern that allows for the delivery of a maximal power density for a specific length of time, a power density can be achieved that does not burn but does consistently stimulate healing in mammals including humans with all skin types and skin presentation regardless of other phenotypic factors. Specifically, skin must undergo an increase in temperature which must be maintained for no less than 45 seconds to achieve a consistent therapeutic effect whereby damaged soft tissue is repaired including being remodeled, including but not limited to the healing of non-inflamed soft tissue.

The energy is delivered by a laser using a handpiece 108 that emits laser energy in a Gaussian pattern (although a pattern with a flat top and other distributions may be utilized). The laser emission is overshadowed by a colored LED marker guide light that substantially or broadly overlays the distribution of the laser energy onto the skin. In the center of this pattern the laser energy is at its highest and it is this area of highest irradiance that provides light energy at a high enough power density to penetrate to the SCNs of the different tissues (e.g., skin, muscle, brain, etc.). The energy is delivered percutaneously, and the way in which the treatment (i.e., the protocol through which the energy is delivered) is precise to access the therapeutic effect as opposed to a generalized tissue heating.

The maximum power density occurs at the center of the laser beam. There is an increase in the temperature of the surrounding tissue due to the specific heat capacity of the tissue. This thermal effect is useful for vasodilation and relaxation of the patient during treatment. However, generalized heating of the skin is not necessary. There is heterogeneity as regards peripheral tissue heating, specific heat capacities of lean and fatty tissues differ, lean tissue typically has a significantly higher specific heat capacity than fatty tissue. The intent of the method described herein is to deliver energy to a SCN. Thus, if the skin is generally warmed then this may limit the ability to achieve the necessary temperature change and provide enough energy to the SCN to result in a consistent effect.

If the necessary power density were applied in a larger beam size, it is likely that the skin would burn. Thus, taking into account the different specific heat capacities, the depths of different SCNs in different tissue types, and the need in all these circumstances to obtain a 10° C. temperature increase for at least 30 seconds, a series of protocols have been developed for optimal treatment of different tissue types and body areas.

Also, when successfully practicing the method of the embodiments described herein, a heat sensation may be felt when being lasered. Specifically, the sensation may linger for one or two seconds after laser exposure has been discontinued. This may be described as heat coming from within the tissue, which is distinct from a superficial heating of the surface of the skin.

In general, the wavelength used in the method described herein is constant, the dose or Joules of energy delivered by the laser are constant (per indication or body area), the essential treatment window is preferably 45 seconds, which is the time that the skin must be maintained with its 10° C. increase, the irradiance and fluence are not a constant but are determined by the tissue and condition to be treated.

In view of this informational background, described and illustrated in more detail hereinafter are exemplary embodiments of a laser-based system 100, along with exemplary embodiments of methods of use of such a system 100 for treating various medical conditions associated with humans. Referring to FIG. 1, there illustrated is a perspective view of the laser-based system 100, according to an exemplary embodiment of the present invention. The system 100 may have a main box or console 104 and a separate ergonomic handpiece 108 connected to the box 104 with a cable 112. The box or console 104 contains most of the components of the system 100, which are described and illustrated in more detail hereinafter. The box 104 and the handpiece 108 (i.e., its outer housing) may each comprise a plastic, a metal, a composite material, or other suitable material.

The system 100 incorporates a therapeutic or medical laser (e.g., main laser module 116 and associated components—FIGS. 3 and 4) that provides laser light for use in the treatment of various medical condition in the human or other mammalian body, according to various innovative treatment protocols or methods some of which are described in more detail hereinafter. In exemplary embodiments, the main laser module 116 includes a laser diode. The user of the system 100 holds the handpiece 108 when applying the treatment laser at a particular location on the patient's body.

The cable 112 may comprise a fiber optic cable together with a plurality of electrical signal wires. The fiber optic cable and the wires may be encased, for example, in a silicone rubber sheath or other suitable material. Note that the terms "cable" and "fiber optic cable" are used interchangeably herein and are both referred to herein using the reference number 112. The fiber optic cable 112 may transmit the laser light beam from the laser light source 116 located inside the box 104 to the handpiece 108 where it is then emitted onto the skin of a patent for treatment of various medical conditions, as described and illustrated in more detail hereinafter. The electrical signal wires may transmit electrical power from the box 104 to the handpiece 108 as well as data signals (e.g., a laser on/off signal) between the box 104 and the handpiece 108. However, it is to be understood that the broadest scope of the laser-based system 100 of the present invention is not limited to having a box 104 separate from the handpiece 108. Instead, the system 100 may have other exemplary embodiments that include a single box 104 for all components including those in the handpiece 108, or more than one box 104 and one or more handpieces 108, including handpieces 108 that are controlled robotically and move autonomously based on predefined algorithms. These alternative embodiments should be apparent to one of ordinary skill in the art in light of the teachings herein.

In an exemplary embodiment, a top surface 120 of the box 104 has a mounting device 124 provided thereon for the handpiece 108 so that the handpiece 108 can be stored or located there for convenience when not in use. Also provided on the top surface 120 of the box 104 is an oval shaped device (not shown) that allows a user to wrap the cable 112 around that device when the handpiece 108 and cable 112 are not in use. In an exemplary embodiment, the fiber optic cable 112 may be approximately 10 feet long. However, the cable 112 may be any desired length in light of the teachings herein. Thus, one end of the cable 112 is connected with the handpiece 108 and the other end of the cable 112 connects with a laser diode 116, or other laser light source, located inside the box 104. The laser diode 116 provides laser light at a particular wavelength (e.g., 1260 nm) that travels through the fiber optic cable 112 and out of the handpiece 108 and onto a human body, as described and illustrated in greater detail hereinafter.

A fiber exit port 128 (FIG. 2) is also located on the top surface 120 of the box 104 in an exemplary embodiment. The fiber exit port 128 provides a stable and secure means for the entire cable 112 (i.e., the fiber optic cable and the electrical signal wires) to pass through the top surface 120 of the box 104 and to the handpiece 108. In general, the fiber optic cable 112 itself is not relatively robust and is prone to failure, primarily through the repeated movement of the cable 112 during normal use of the handpiece 108. To be suitable for medical applications, the box 104 must act as a Faraday cage to shield electromagnetic fields. In the prior art, it is known to have the fiber optic cable screw and unscrew to a port located on the outside of the box. However, when the fiber optic cable is detached from the box in this manner, there is static that attracts dust both to the port and to the end of the fiber. If the dust is not cleaned off adequately, it acts as a focus for energy and the fiber optic cable or port may catch fire. It is known to use a fiberscope, which is essentially a handheld microscope, that allows someone to see the end of the fiber optic cable and clean off any dust particles using an alcohol swab. However, in practice it has been shown that there is no way to adequately clean the port using the fiberscope.

Embodiments of the present invention mitigate this problem by having the fiber optic cable 112 (which is part of the entire cable 112) running directly from its connection with the diode and out through the box 104 at the fiber exit port 128, eventually ending up in the handpiece 108. This eliminates the need for a fiberscope and the relatively high failure rate inherent with the screw on/screw off type of external port requirement. Nevertheless, the fiber optic cable 112 must exit the box 104 without breaching the Faraday cage.

Figure 2:
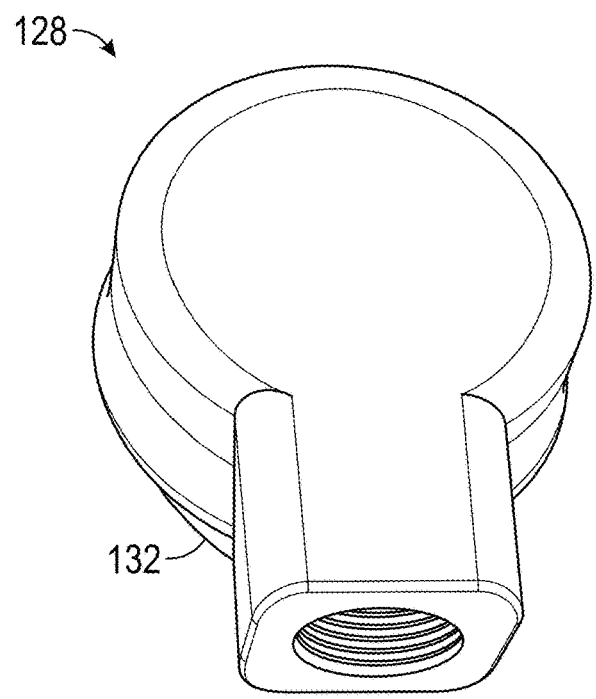
FIG. 2 is a perspective view of a fiber exit port that is part of the laser-based system of FIG. 1, according to an exemplary embodiment of the present invention.

Referring also to FIG. 2, there illustrated in greater detail is a portion of the specialized fiber exit port 128 for the cable 112. Certain components of the fiber exit port 128 may be made of Delrin® or other suitable material. A base 132 of the fiber exit port 128 is placed within a hole (not shown) formed in the top surface 120 of the box 104, to thereby allow access to the inside of the box 104. The base 132 may have outer threads formed thereon which may be secured by a corresponding nut and washer located inside the box 104. Also, the fiber exit port 128 may swivel at a total exemplary circular angular amount of 270 degrees to thereby allow the cable 112 to move with the user of the system 100 when the user is manipulating the handpiece 108 for treatment of a human.

The inside of the fiber exit port 128 may be coated with a conductive material to allow for a relatively low and safe amount of radio frequency emissions from the box 104 as the system 100 is used in medical environments. The internal structure of the fiber exit port 128 comprises an empty channel or void that is wide enough to allow the cable 112 to pass through, but not so wide as to allow emissions to pass through. Further, a relatively small amount of copper mesh may be included around the cable 112 at the base 132 of the fiber exit port 128 located inside the box 104. This is done to ensure that any EMC/EMI emissions are controlled to a minimum amount and to an amount below the threshold requirements of the FDA and any other regulatory body that controls and regulates medical devices. The cable 112 may be attached to the fiber exit port 128 on the outside of the box 104 such that a strain relief for the cable 112 is provided. The fiber exit port 128 provides for a secure and lasting connection of the cable 112 within the box 104 and through the hole in the box 104, as the cable 112 is moved about during use of the handpiece 108.

The box 104 has been described hereinabove with having its top surface 120 include the fiber exit port 128, the mounting device 124 that holds the handpiece 108, and the device that the fiber optic cable 112 is wrapped around for holding or storage. However, it should be understood by one of ordinary skill in the art that one or more other surfaces of the box 104 (e.g., the back of the box or either side of the box) may have located thereon the fiber exit port 128, and/or the mounting device 124 that holds the handpiece 108, and/or the device that the fiber optic cable 112 is wrapped around for holding or storage. Further, the fiber exit port 128, the mounting device 124 that holds the handpiece 108, and the device that the fiber optic cable 112 is wrapped around do not all have to be located on the same surface of the box 104. For example, if none of these devices are located on the top surface 120 of the box 104, then the box 104 needs a lesser amount of height when located on a shelf or a storage area.

Figure 3:
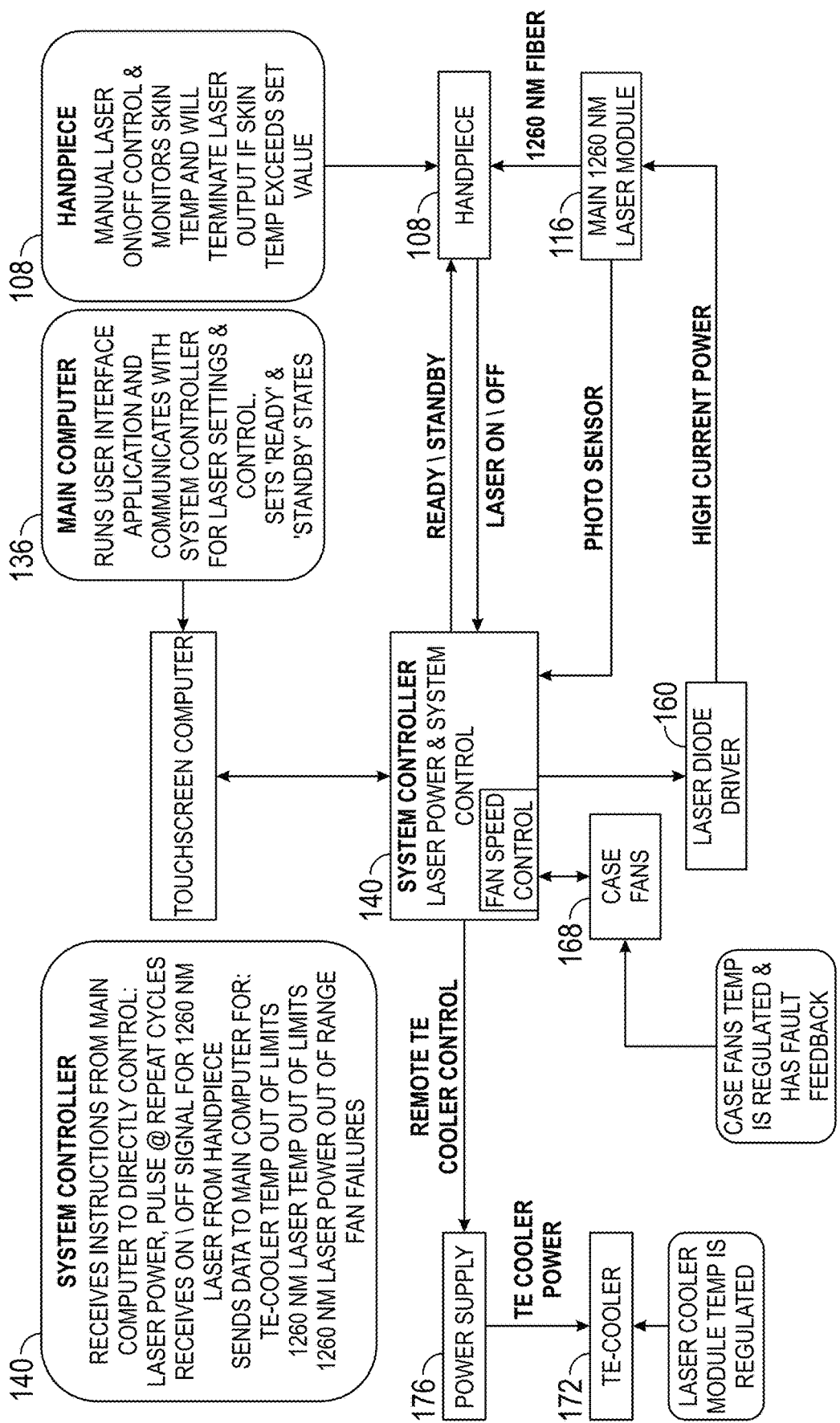
FIG. 3 is a first block diagram of the laser-based system of FIG. 1 showing various components located mostly in a box portion of the laser-based system, according to an exemplary embodiment of the present invention.
Figure 4:
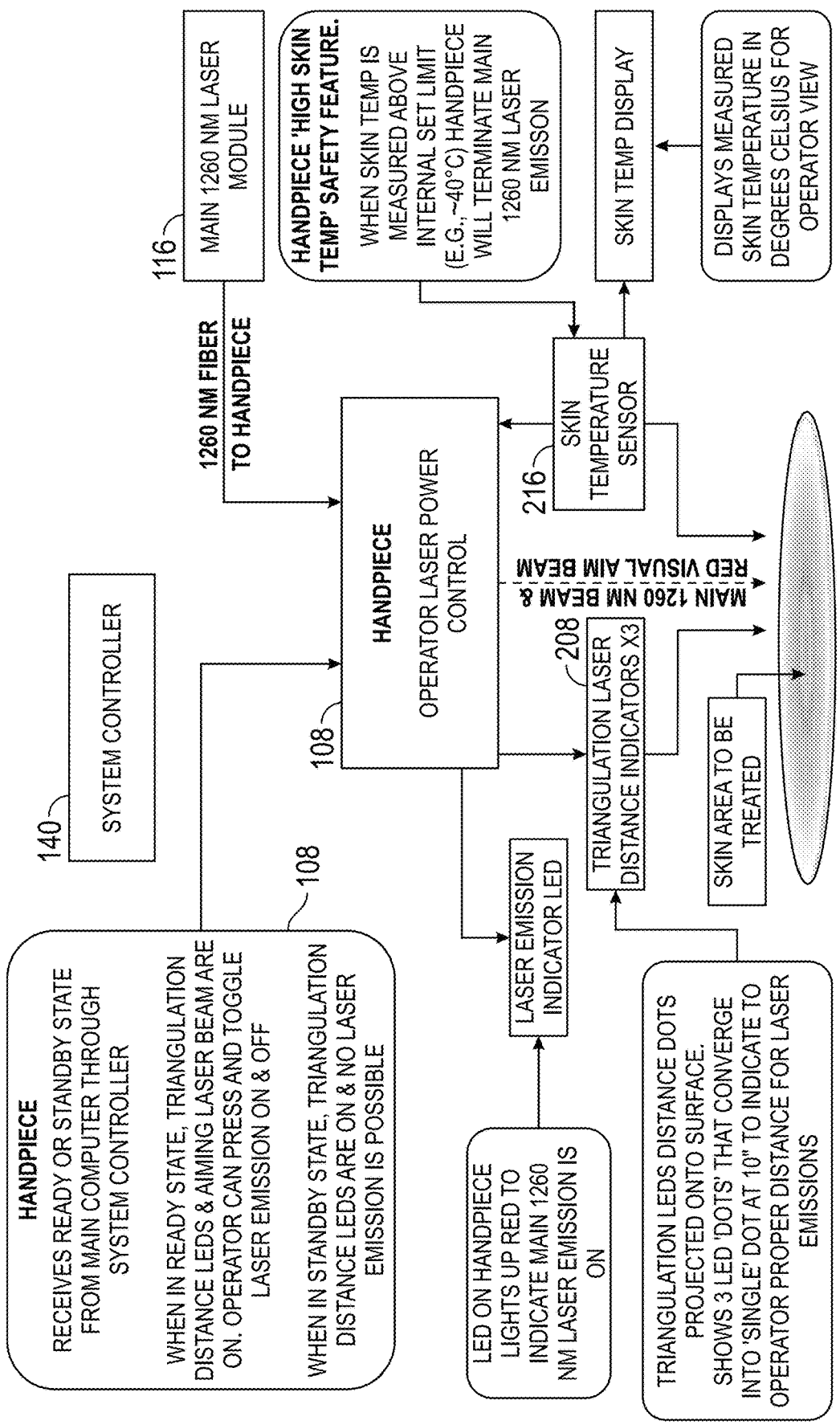
FIG. 4 is a second block diagram of the laser-based system of FIG. 1 showing various components located mostly in a handpiece portion of the laser-based system, according to an exemplary embodiment of the present invention.
Figure 5:
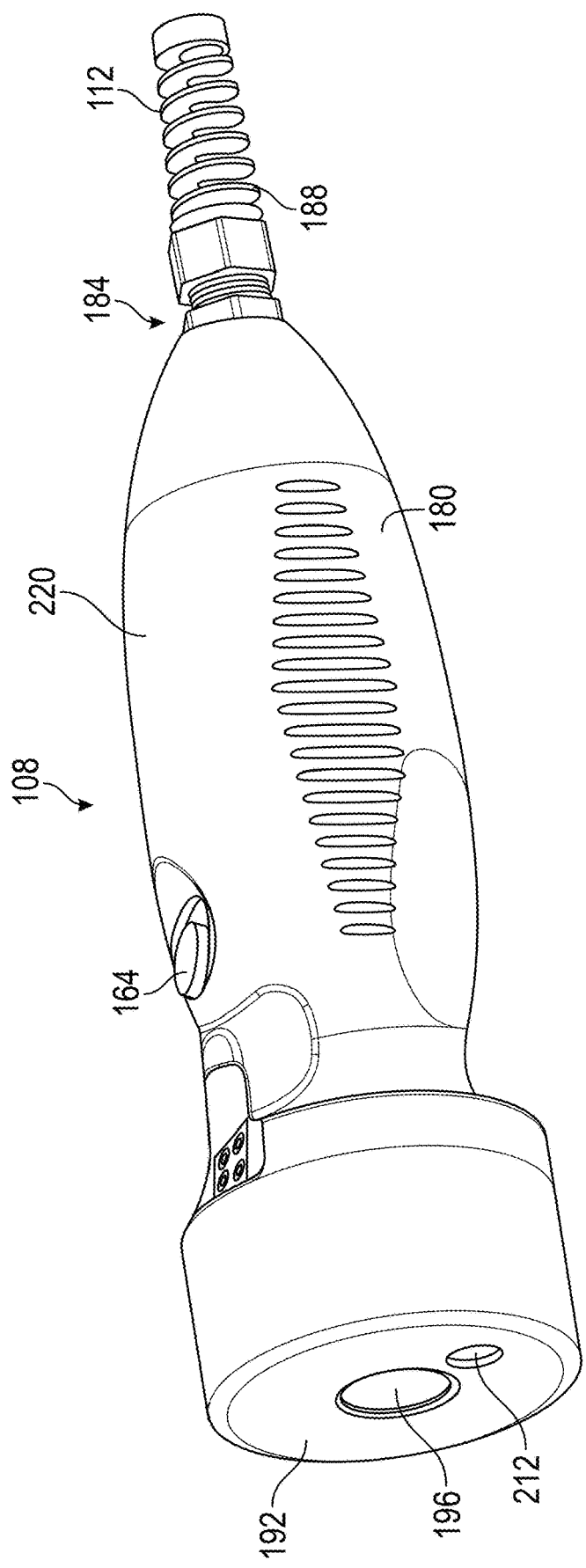
FIG. 5 is a perspective view of the handpiece of the laser-based system of FIG. 1, according to an exemplary embodiment of the present invention.
Figure 6:
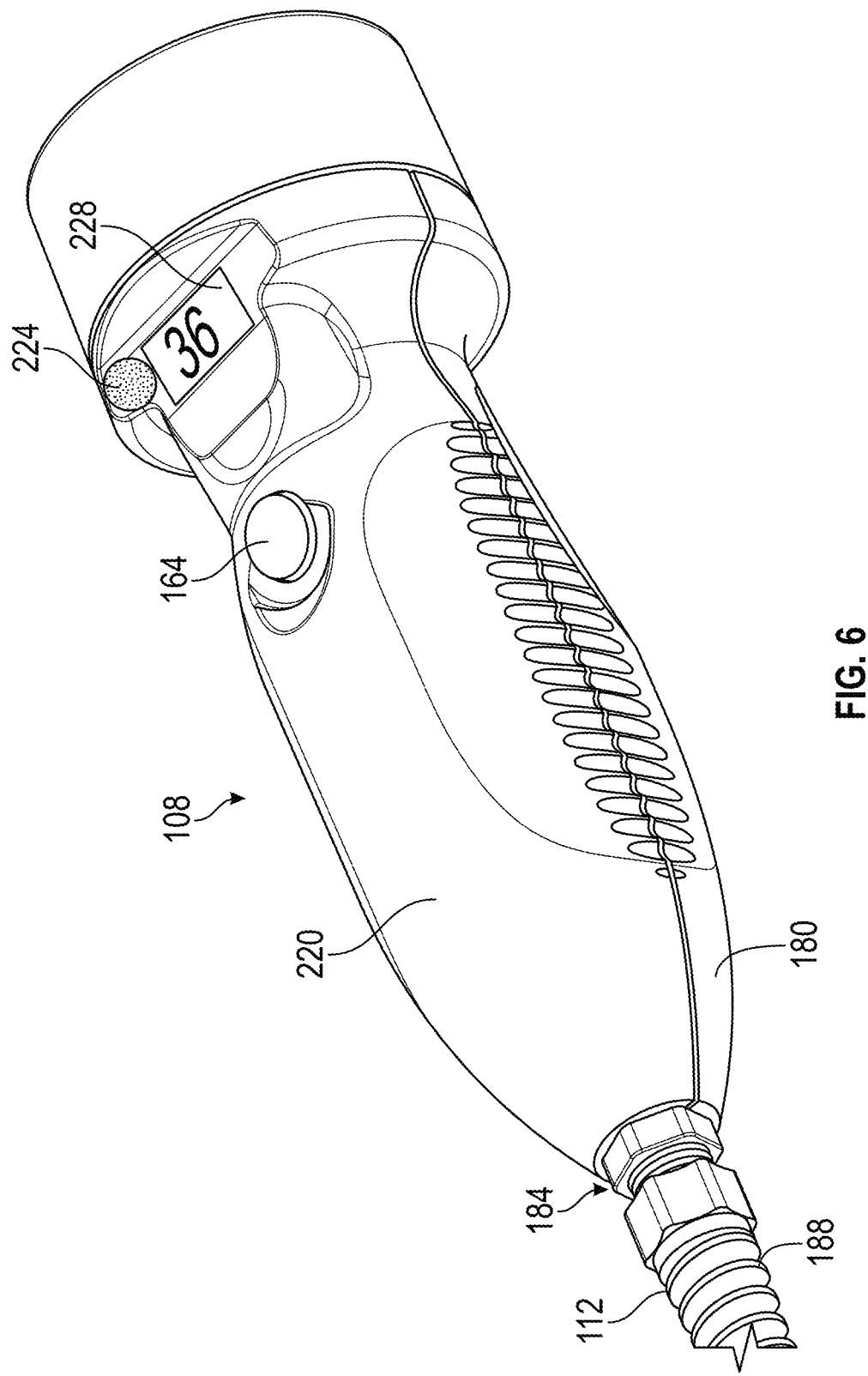
FIG. 6 is a top view of the handpiece of FIG. 5, according to an exemplary embodiment of the present invention.

Referring to FIGS. 3 and 4, there illustrated are block diagrams of various components that comprise the laser-based system 100 of FIG. 1, according to exemplary embodiments of the present invention. FIG. 3 illustrates various components located mostly in the box 104, while FIG. 4 illustrates various components located mostly in the handpiece 108.

The treatment laser may comprise a commercially available diode laser located within or as a part of the main laser module 116 (i.e., a Fiber Coupled Laser Module) together with its associated components. According to exemplary embodiments of the present invention, the treatment laser 116 is preferably operated at a wavelength of 1260 nm, which is within the near IR range. This is to take advantage of the various medical benefits from a laser 116 operated at 1260 nm, as discussed in detail hereinbefore. The laser 116 may have an approximate tolerance wavelength bandwidth of plus or minus 15 nm, which is typical of modern diode lasers.

The box 104 may contain various other components associated with the operation of the laser-based system 100. These components may include, for example, a main computer 136 and a system controller 140. The system controller 140 may comprise an embedded microprocessor signal processing device or similar device that controls and reads data from the various peripheral devices associated with the laser-based system 100, as described and illustrated in more detail hereinafter (e.g., USB memory, switches, drivers, sensors, etc.). The main computer 136 may be part of a commercially available medical certified tablet computing device. As such, the medical tablet device also includes a combination touchscreen display and input panel 144 that allows the user to provide various inputs to the system 100 by touching the input panel 144 with a finger or a stylus. The touchscreen display 144 conveys visual information to the user regarding various operating parameters and modes of operation of the laser-based system 100. Audible information may also be provided to the user.

On a front panel 148 of the box is located a pushbutton switch 152 that allows a user to turn the system 100 on and off for normal operation. The front panel 148 may also contain a pushbutton power emergency shutoff switch 156 that allows a user to quickly terminate all operation of the treatment laser system 100 in the event of an emergency which occurs during operation of the device 100. A top, back, or side panel or of the box 104 may have a hole that acts as part of the fiber exit port 128 for the cable 112 to be connected inside of the box 104, as described and illustrated in more detail hereinbefore with respect to FIGS. 1 and 2.

Located inside the box 104 is the main computer 136 and the system controller 140 and their associated components. The main computer 136 runs the primary software program of the system 100, where the primary software program is stored in memory that is a part of the main computer 136. Also, since the main computer 136 is part of the medical tablet device in an exemplary embodiment, the main computer 136 also runs a user interface software application program associated with operation of the touchscreen display and input panel 144. That is, the main computer 136 processes the user input signals from the touchscreen display and input panel 144 and provides signals to the touchscreen display and input panel 144 for visual display to the user of various system operating parameters (i.e., the graphical user interface or "GUI"). The user input signals relate to e.g., control of the laser 116 by the user for treatment. The main computer 136 also sends and receives signals indicative of data and instructions to and from the system controller 140. The data and instruction signals relate to settings and control of the laser 116, for example, the "READY" and "STANDBY" states of the laser 116 (which the main computer 136 may set), the amount of power to be applied by the laser 116 during treatment (e.g., between 2 Watts and 60 Watts), and the mode of operation of the laser 116 (e.g., continuous, interval/pulsed, or custom, and if custom mode then the number of repeat cycles).

The system controller 140 communicates using electrical signals with the main computer 136, the handpiece 108, the laser 116, and with other components inside the box 104. For example, the system controller 140 responds to a signal from a photo sensor (e.g., a photo diode detector) located within the laser module 116. The photo sensor detects the amount of light scattered from the laser light beam output from the laser module 116. Thus, this signal from the photo sensor indicates the amount of power being output from the laser 116 at any moment in time. As a result, this signal may be used by the system controller 140 for calibration of the amount of power output from the laser light module 116. This signal may also be provided by the system controller 140 to the main computer 136 to indicate that the amount of power provided by the laser 116 is outside of an acceptable range. Another signal may be provided by the system controller 140 to the main computer 136 that indicates when the temperature of the laser module 116 is outside of an acceptable range.

The system controller 140 controls operation of a commercially available laser diode drive device 160 that provides the electrical power to the laser 116 for its operation. For example, the system controller 140 may receive an "ON/OFF" signal from the handpiece 108 that is indicative of a desire by the user to start or stop operation of the laser 116 for treatment. This signal may be initiated by the user through use of a pushbutton switch 164 (FIGS. 5-8) located on the handpiece 108. The system controller 140 then controls operation of the laser diode drive device 160 and the laser 116 accordingly. For example, the mode of operation of the laser 116 may be controlled between continuous mode, interval/pulsed, or custom mode. Power pulsing may also be a possibility. Generally, diode lasers may be operated in a super pulse mode know as quasi-cw operation. This allows more diode drive current to be applied for brief pulses or pulse trains. The higher-powered pulse provides more heating power at greater depths of tissue.

The box 104 may also contain one or more cooling fans 168 for cooling the temperature inside the box 104. The speed of these case cooling fans 168 may also be controlled by the system controller 140 to regulate the temperature inside the box 104 and provide for fault feedback associated with fan operation. The system controller 140 may provide a signal to the main computer 136 to indicate that a fan failure condition exists.

The system controller 140 also controls a thermo-electric (TE) cooler device 172 inside the box 104 that controls the temperature of the laser 116 to be within an exemplary temperature range of between 18° C.-32° C. (approximately 64° F.-90° F.). The thermo-electric cooler 172 may comprise a commercially available device that may operate on convective cooling principles. The system controller 140 may continuously monitor the temperature of the laser 116 as that signal is provided by the diode laser module 116. The thermo-electric cooler 172 may be physically located directly underneath the laser module 116 inside the box 104. The laser 116 is turned off by the system controller 140 if the temperature of the laser 116 exceeds the upper limit. The system controller 140 may provide a signal to the main computer 136 to indicate that the temperature of the thermo-electric cooler 172 is outside of an acceptable range or above an acceptable value.

A power supply 176 inside the box 104 provides electrical power to the thermo-electric cooler 172. The power supply 176 may comprise a commercially available device which provides 450 Watts of power. The system controller 140 may control the operation of the power supply 176 such that the power supply 176 is turned on and off as required for provision of electrical power to the thermo-electric cooler 172.

Referring to FIGS. 5-9, there illustrated are various views of the handpiece 108 of the laser-based system 100 of FIG. 1. In exemplary embodiments of the laser-based system 100 of the present invention, the handpiece 108 is of a lightweight, ergonomic design, having various contours formed in an outer surface of the housing 180 of the handpiece 108. The various contours allow for the handpiece 108 to be gripped and held by the user in various orientations with maximum comfort and control by the user's hand. This design also allows the handpiece 108 to sit comfortably in the user's hand, which makes use of the treatment laser 116 (i.e., "lasering") for long periods of time comfortable and tolerable for the user. The housing 180 may comprise two separate sections or pieces of plastic or other suitable material that fit together and are held together with screws.

At an "entrance" end 184 of the handpiece 108, the cable 112 enters the inside of the housing 180. The optical fiber portion of the cable 112 is secured within the handpiece 108 by an SMA connector that is connected to a corresponding SMA connector housing which is secured to the inside of the housing 180. The cable 112 is also secured to the handpiece 108 at the entrance end 184 of the housing 180 by a strain relief 188 or similar device. The strain relief 188 may snap in place into the housing 180. In an exemplary embodiment, the cable 112 may be approximately 10 feet long, and the fiber optic portion of the cable 112 may be such that it transmits the laser light therethrough at the selected wavelength of 1260 nm. The electrical signal wires within the cable 112 may connect inside the housing 180 at the appropriate physical locations using suitable connections. When the laser-based system 100 is not in use, the 10-foot cable 112 may be stowed, for example, by wrapping the cable 112 around the oval-shaped device as shown in FIG. 1.

The opposite end of the handpiece 108 may have a relatively flat surface 192 that faces the skin of the patient during operation of the laser-based system 100 of embodiments of the present invention. The flat facing surface 192 has several holes formed therein (see FIG. 7). A centrally located round aperture or hole 196 may contain a lens or lens system through which the treatment laser beam emanates out of the handpiece housing 180 in a proper cone of radiation 200 (FIG. 8) during use of the laser 116 for treatment (i.e., for pointing at the area of the skin of the patient to be treated). In the alternative, the centrally located round aperture or hole 196 may not utilize a lens. The cable 112 may be disposed within the handpiece housing 180 such that the end of the cable 112 is abutting an inside surface of the flat facing surface 192 where the laser light beam exits the handpiece housing 180. As such, the possibility of the laser light causing unwanted heating of the inside of the handpiece housing 180 is minimized.

As mentioned hereinabove, the laser light energy may be delivered by the laser 116 in a Gaussian pattern or in a pattern with a flat top or other distribution. The laser-based system 100 may include the option of switching between a peaked Gaussian energy profile over the treatment area and a uniform energy distribution. This may be accomplished by incorporating a rotating optic holder containing either a lens for Gaussian or a diffractive optic for uniform beam profiles. Using the diffractive optical elements, the shape of the treatment may be switched between round, square, or rectangular.

In addition, the treatment laser light beam diverges from the main or central aperture 196 of the handpiece 108 and expands to a diameter of approximately 3 inches at the treatment site. The beam continues to diverge once the light enters through the patient's skin. Thus, the energy density per unit area is reduced significantly depending on the depth through the tissue to the inflamed or injured site. Also, the energy may be concentrated or focused such that more energy is delivered directly to the injured tissue which may be well below the surface of the skin while at the same time keeping the energy density low enough at the surface of the skin to prevent patient discomfort.

Figure 7:
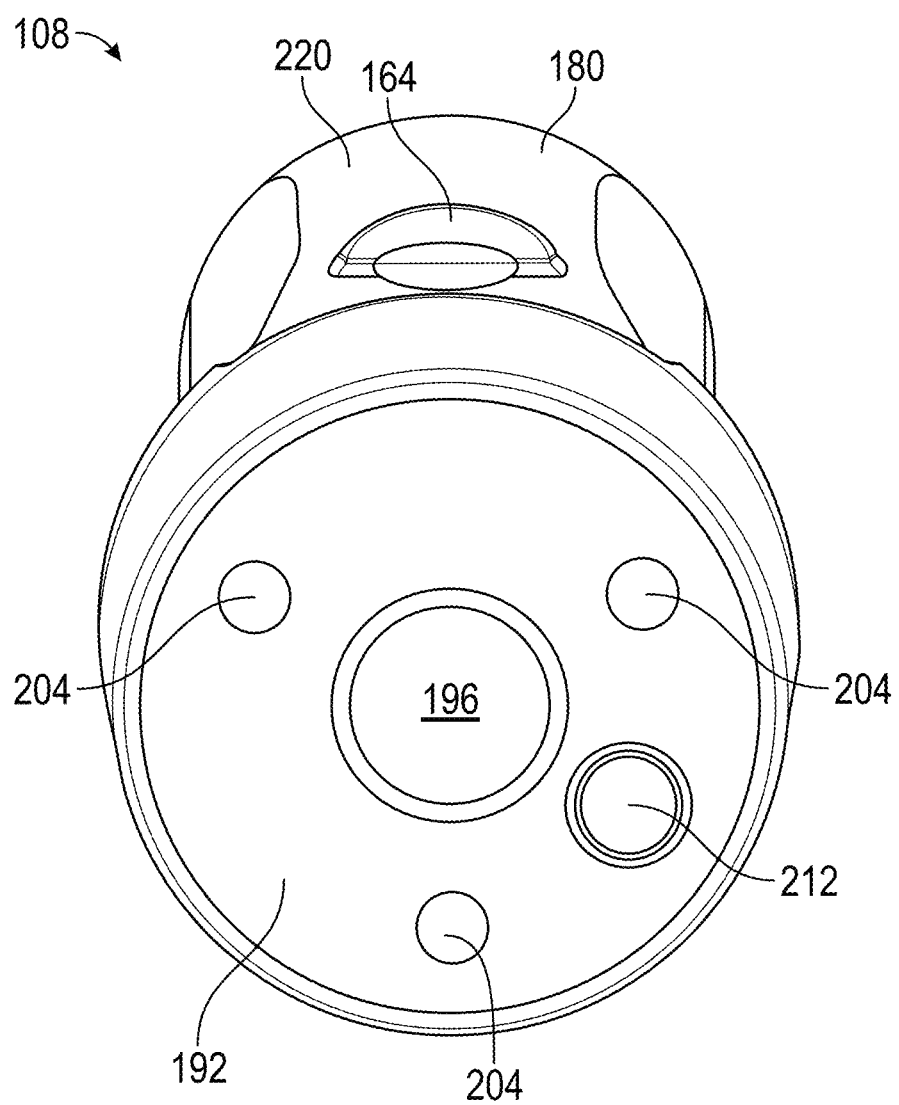
FIG. 7 is a view of a front face portion of the handpiece of FIG. 5, according to an exemplary embodiment of the present invention.
Figure 8:
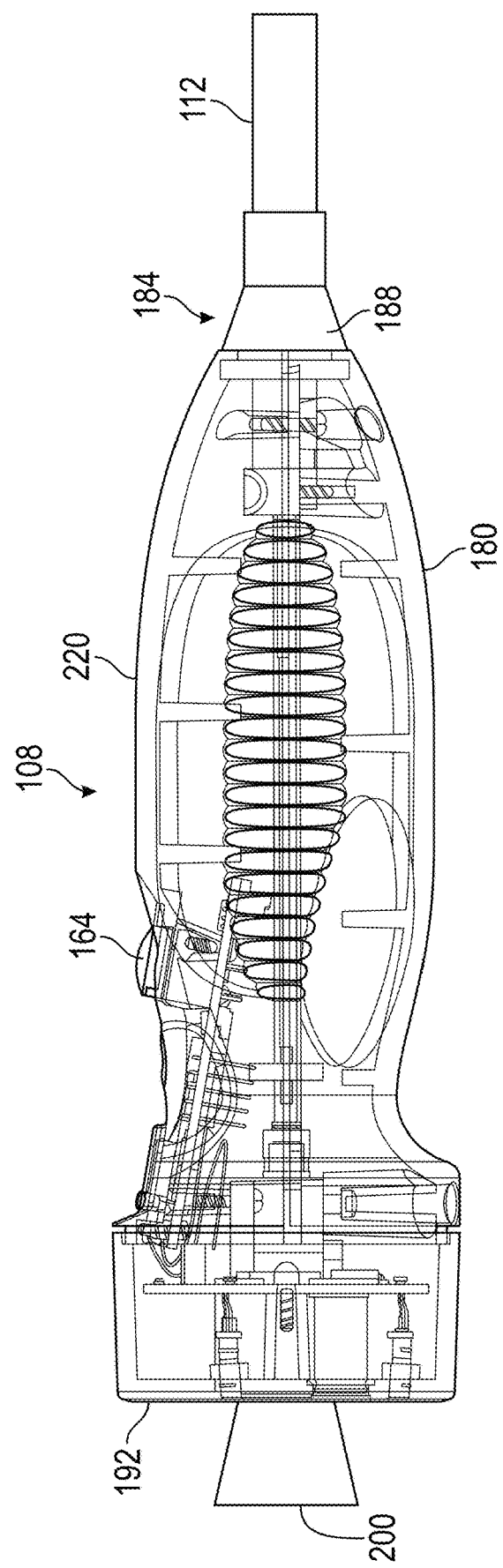
FIG. 8 is a sectional and cut away view of the handpiece of FIG. 5, according to an exemplary embodiment of the present invention.
Figure 9:
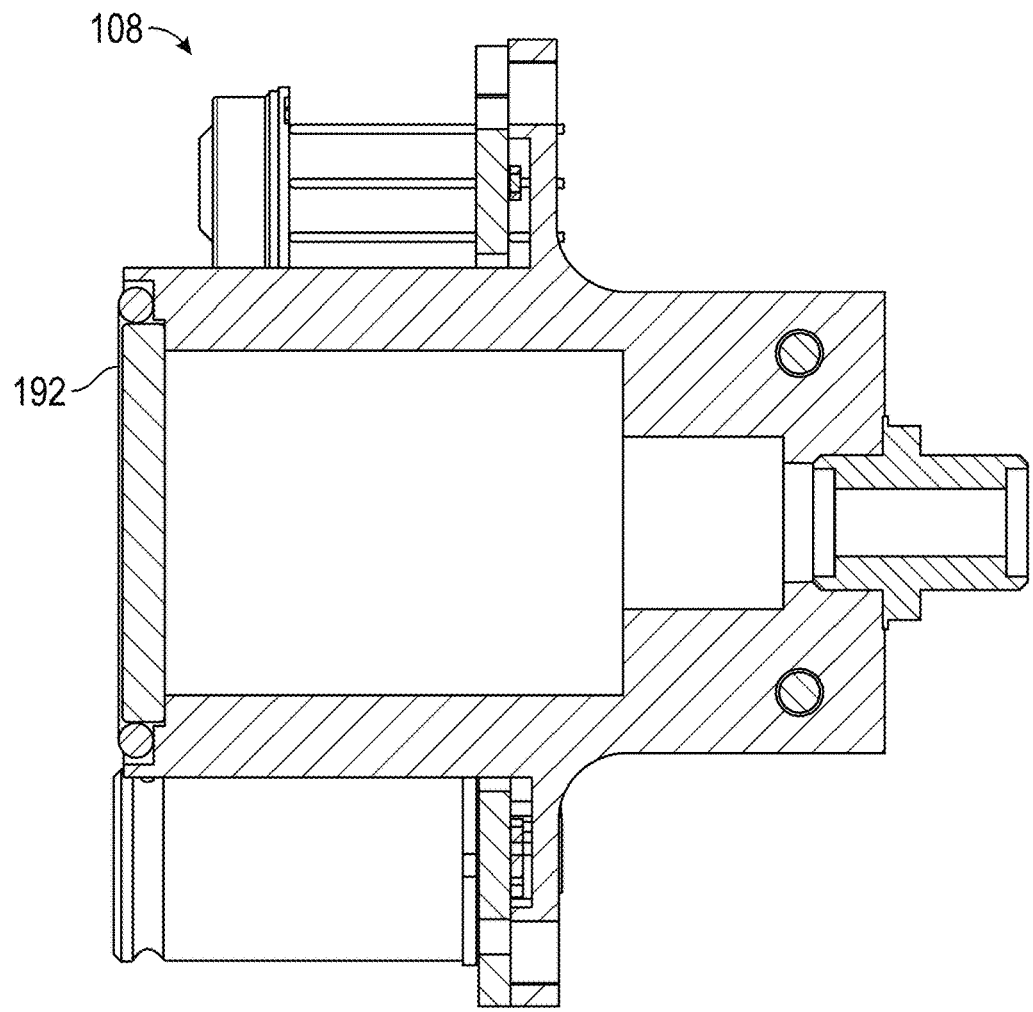
FIG. 9 is a detailed view of several of the component modules within the handpiece of FIG. 5, including the Fiber Cell, Skin Temp Sensor, and Aiming Laser Modules, according to an exemplary embodiment of the present invention.

Three smaller diameter, round apertures or holes 204 are located at approximate equal distances or angular spacings (i.e., 120 degrees) in and around the flat facing surface 192 of the handpiece 108 (see FIG. 7). In accordance with exemplary embodiments of the present invention, each of these three apertures 204 allows for a distance measuring laser light beam to exit the handpiece housing 180 and be directed at the skin of the patient being treated by the laser-based system 100 of the present invention, as described and illustrated in greater detail hereinafter. The three aiming laser beams may be red in color and may be provided by appropriate laser diode pointer modules 208 located inside the handpiece housing 180. Each module 208 may operate similar to a time of flight (TOF) module.

The three or triangulation laser beams are arranged such that they converge together into a single "dot" or "spot" at a predetermined distance (e.g., 10 inches) away from the flat facing surface 192 of the handpiece housing 180. This distance is a desired and proper distance for a user to hold the handpiece 108 away from the skin of the patient for proper operation of the laser-based system 100 of the present invention. Thus, this single laser light beam spot or dot provides a visual indicator to the user of the handpiece 108 for proper distance orientation thereof as well as proper spatial orientation thereof (i.e., aiming of the treatment laser beam).

Another aperture or hole 212 is formed in the flat facing surface 192 of the handpiece housing 180. This aperture 212 may accommodate a skin temperature thermal sensor 216 (FIG. 4) that is used to measure the skin temperature of the patient using reflected light while the treatment laser 116 is being operated. The skin temperature sensor 216 may operate in real-time. As such, a shut off may be included within the laser-based system 100 of embodiments of the present invention such that if the skin temperature of the patient exceeds a certain amount or threshold value (e.g., 45° C. or 113° F.), the treatment laser 116 then ceases operation to prevent any damage to the patient's skin or underlying tissue. In addition, this skin temperature sensor 216 may be used to warn the operator before reaching the "high temperature" or "over temperature" state.

Inclusion of a skin temperature sensor 216 in the handpiece 108 provides a number of advantages over the prior art. For example, the sensor 216 allows for the application of the laser 116 to areas of the skin having tattoos without burning of the skin. The temperature sensor 216 will cut off or stop the application of the laser light when the reflected skin temp, as measured by the sensor 216, gets close to a threshold for potential burning of the skin. Different dyes are commonly used in tattoos, and there is no certain way to know the pigments used in those dyes. Yet, it is known that these dyes absorb energy differently. In the prior art, the only way to laser over a tattoo is to cut the energy level of the laser, because otherwise there is heat absorption and skin damage will result. This means that therapeutic doses of energy cannot be reached with prior art lasers-based medical devices. The best one can achieve with such prior art devices is to heat the upper 5 mm of the skin to the point of discomfort for the patient. In contrast, the peak of the laser beam of embodiments of the present invention is narrow enough such that the user can go around the edge of a tattoo or a mole if desired. As such, the skin temperature sensor 216 will keep the laser light beam safe around tattoos and moles. The skin temperature sensor 216 also allows for lasering of people with impaired sensation.

Although not shown in the Figures, yet another aperture or hole may be formed in the front face 192 of the handpiece 108 to accommodate a thermal camera located inside of the handpiece 108. The thermal camera may provide a real time picture of the treatment site with corresponding temperature profiles over the skin surface. As such, this would provide visual feedback to the user of either hot spots which are being created with the laser or low energy density zones. Small thermal cameras are commercially available that are both physically small and low cost.

Further, active skin cooling may be possible, however, the resulting complexity of the laser-based system 100 would likely increase. Thus, higher energy densities for the treatment laser 116 may be employed while keeping the skin at a comfortable temperature.

On a generally upper or top surface 220 of the handpiece housing 180 is disposed the pushbutton switch 164, which is used to turn on the treatment laser 116 for application of the laser 116 to the skin of the patient. This switch 164 allows the laser 116 to be switched on and off from the handpiece 108. In an exemplary embodiment, the user must depress or "tap" the pushbutton switch 164 to turn on the treatment laser 116. Thus, once the pushbutton switch 164 is not depressed or engaged, the treatment laser 116 remains on. A single press or "tap" of the pushbutton switch 164 will then turn the laser off. As such, the pushbutton switch 164 operates as a toggle switch. Also, the pushbutton switch 164 may have a cover to prevent inadvertent operation of the switch 164.

Also located on the upper or top surface 220 of the handpiece housing 180, e.g., near the pushbutton on/off switch 164, is an LED 224 (FIG. 6) or similar visual lighting device. The LED 224 lights up when the treatment laser 116 is actively "ON" and does not light up when the treatment laser is "OFF." Thus, the LED 224 provides the user of the handpiece 108 with a visual indicator that the treatment laser 116 is emanating laser light.

Also disposed on the upper or top surface 220 of the handpiece housing 180 next to the LED 224 is a two-digit or three-digit numerical indicator 228, which provides a visual indication of the then-current skin temperature of the patient as measured or sensed by the skin temperature thermal sensor 216 on the front face 192 of the handpiece 108. The skin temperature may be displayed on the indicator 228 in degrees Celsius or Fahrenheit and may be toggled therebetween.

In exemplary embodiments of the present invention, in operation the handpiece 108 allows the treatment laser beam to be directed in a proprietary sequence to different locations on the human body. To this end, the handpiece 108 receives the "READY" and "STANDBY" signals from the main computer 136 through the system controller 140. When the laser-based system 100 is in the "READY" state, the three or triangulation distance lasers 208 and the resulting aiming beam are on. This allows the user to then activate the treatment laser 116 by depressing the pushbutton switch 164 on the top surface 220 of the handpiece 108. In contrast, when the laser-based system 100 is in the "STANDBY" state, the three or triangulation distance lasers 208 and the resulting aiming beam are off, and no emission of the treatment laser 116 by the user is possible.

The various components disposed within the handpiece housing 180 may be mounted on one or more circuit boards and/or to the inside of the housing 180 and may be connected using ribbon cable electrical connectors and/or with electrical wires.

Figure 10:
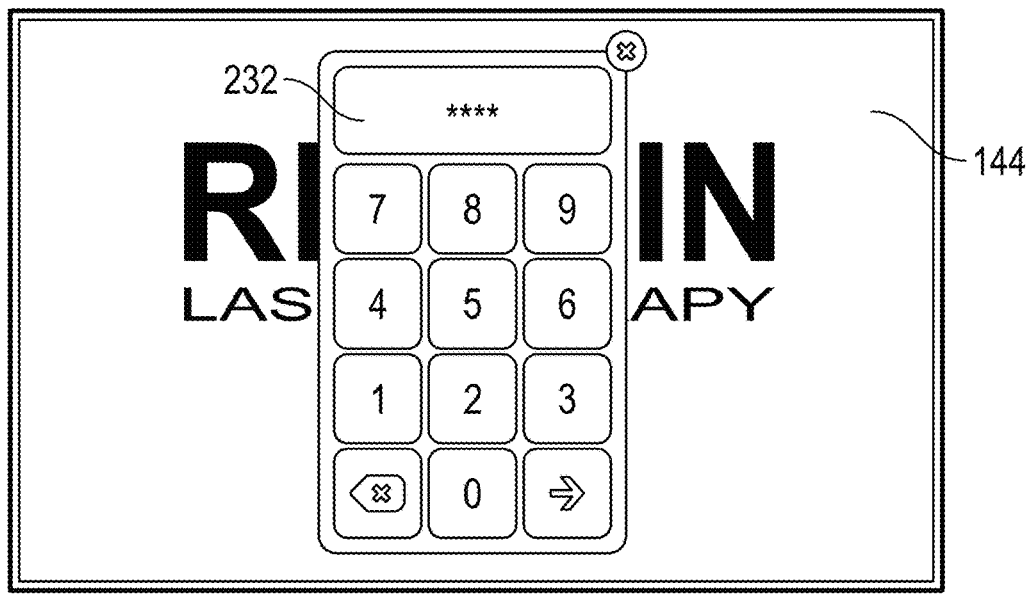
FIGS. 10 and 11 are two different front views of a touchscreen display and input panel of the laser-based system of FIG. 1, which show two different examples of information and data being visually displayed to the user of the system, according to exemplary embodiments of the present invention.
Figure 11:
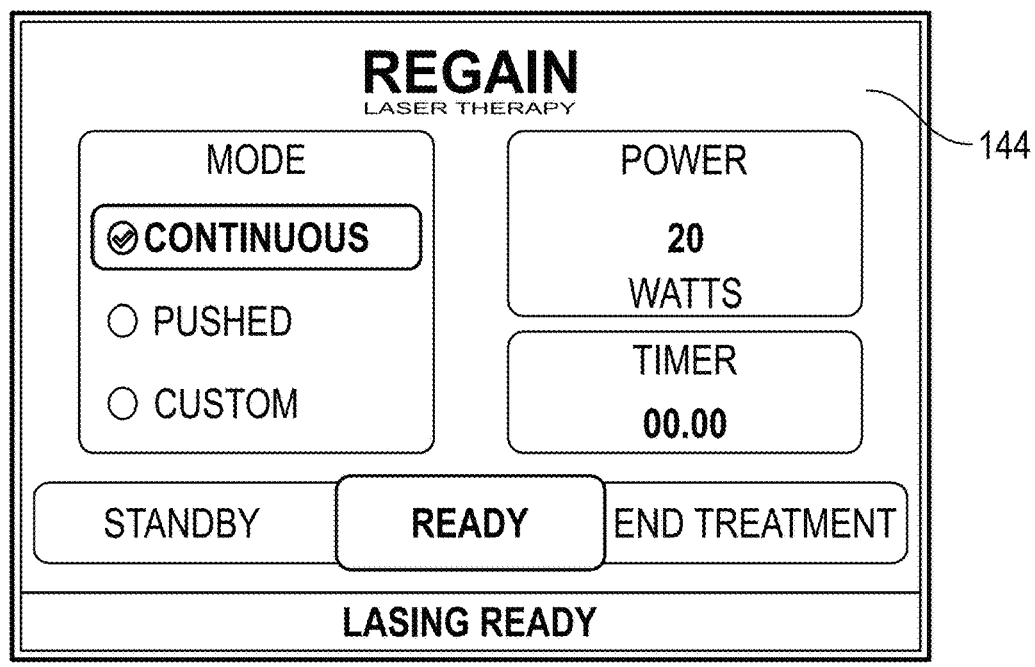

Referring to FIGS. 10 and 11, there illustrated are two different front views of the touchscreen display and input panel 144 which show two different examples of exemplary information and data being visually displayed to the user and prompting input by the user during operation of the laser-based system 100 of FIG. 1. The information and data relate to various operating modes and operating parameters of the system 100.

In operation of the laser-based system 100 of exemplary embodiments of the present invention described in detail hereinabove and illustrated in FIGS. 1-9, a user starts the system 100 for operation by activating the power pushbutton switch 152 on the front panel 148 of the box 104. The system 100 may then perform some initial checks of the various system components and software to verify their proper operation and communication with one another. Once the initial checks have been completed, the user may then be prompted to enter a pre-programmed multiple digit code (e.g., 4 digits) to be able to access and operate the system 100. This is so that only predetermined authorized users are able to operate the system 100. Thereafter, the user may operate the treatment laser 116 to treat a patient. This may be done by the user selecting the mode of operation of the system 100 which determines the type of laser light to be applied to the patient (e.g., continuous, interval/pulsed, or custom), the power level of the applied laser light in Watts, and the duration of time that the laser is applied to the patient.

During operation of the laser-based system 100, an activity log may be kept and updated and stored in memory by which all of the various different operations performed by the system 100 are stored for future reference. If, at any time during operation of the system 100, a malfunction occurs (e.g., the temperature of the laser 116 exceeds an upper threshold value), then system operation will cease and the appropriate error messages will be displayed to the user on the touchscreen display and input panel 144 so that corrective action can be taken by the user.

In FIG. 10 is an illustration of the touchscreen display and input panel 144 which shows a numerical keypad 232 being visually displayed to the user so that the user can use his/her finger, a stylus, or other device to enter the pre-programmed 4-digit numerical code or passcode unique to that user, which then allows the user to access and operate the system 100. If the user enters an incorrect passcode, an error message will be displayed on the touchscreen display 144. This type of numerical keypad entry screen may be used in various other operational events during operation of the system 100 to allow the user to enter numerical information.

Once the user enters the correct passcode, the touchscreen display and input panel 144 may then transition to a treatment mode setup screen in which the user is prompted to enter the desired mode of operation of the laser-based system 100 along with various parameters with respect to the selected mode of operation. In exemplary embodiments of the laser-based system 100 of the present invention, the modes of operation of the treatment laser may comprise continuous, interval/pulsed, or custom. In general, in continuous mode, the laser 116 may be operated at a selected power level for a predetermined total period of time. In interval/pulsed mode, the laser 116 may be operated at predetermined alternating periods of on time and off time for a predetermined total period of time. In custom mode, the laser 116 may be operated at user selected alternating periods of on time and off time for a user selected total period of time. For any of these modes of operation of the treatment laser 116, the user may select the power level of the laser 116 to be within the available range of, e.g., 2 Watts to 60 Watts.

Once the user has selected the mode of operation of the laser 116 and its associated parameters, the laser-based system 100 may transition to an operation state in which the system 100 is ready to allow the user to apply the treatment laser 116 to the skin of the patient. In FIG. 11 is an illustration of the touchscreen display and input panel 144 which shows various items of information and data visually displayed to the user. This information includes the selected mode of operation (e.g., continuous), and power (e.g., 20 Watts), along with the timer being set to zero in anticipation of the timer counting time once treatment with the laser begins. In addition, the "READY" visual indicator may be in red and be solid and non-blinking, and a "LASING READY" bar in red may be provided across the bottom of the screen. This indicates to the user that the treatment laser 116 is ready to be used on a patient. The user can hit the "END TREATMENT" display bar to stop treatment with the laser 116.

The visual displays of FIGS. 10 and 11 are typical of the exemplary displays of information and data provided to the user of the laser-based system 100 on the touchscreen display and input panel. As mentioned, some of these displays require input by the user on the touchscreen display and input panel. Displays of information and data for the other modes of operations (i.e., interval/pulsed and custom) and their associated parameters should be apparent to one of ordinary skill in the art in light of the teachings herein.

It should be understood by those of ordinary skill in the art that the embodiments of the laser-based system 100 of the present invention described hereinabove and illustrated in FIGS. 1-9 are purely exemplary and do not necessarily define the broadest scope of the present invention. As such, there are many other alternative ways to embody the box 104 and the handpiece 108 including their respective components and functionality in keeping with the broadest scope of the present invention, which should be readily apparent to those of ordinary skill in the art in light of the teachings herein.

Referring to FIGS. 12-18, a general approach to achieving a consistent positive outcome for treating soft tissue injuries is now described and illustrated. The laser-based system 100 described and illustrated herein can be used to treat relatively large areas of the human body, such as the back and shoulders, hamstrings, and quadriceps. The laser-based system 100 can also be used to treat smaller, more discrete areas of the human body, such as the sinuses, the hand, and the foot. However, the general principles for treating all these areas are the same. That is, the dose of laser light energy delivered to the tissue has to be high enough to overcome the energetic threshold and activate healing without causing thermal damage. This requires systematic management of the power density of the laser light to enable delivery of an appropriate dose of laser light energy to the affected area of the body without causing thermal damage to the skin and tissue. FIG. 19 is a table showing the resulting power density of the laser 116 of the laser-based system 100 of FIG. 1 with other system parameters being varied, according to exemplary embodiments of the present invention.

The general approach is to treat the specific area of damaged tissue, together with an approximate 20% margin outside of that specific area. This is done by administering the laser light energy in a non-overlapping pattern with respect to the centers of the applied laser beams. In an exemplary embodiment, the front face 192 of the handpiece 108 is placed approximately 10 inches from the targeted area of the skin. The table of FIG. 19 shows the resulting laser beam size and laser power density. The laser light delivers its energy in a Gaussian fashion with the center of the beam circle being the peak or highest amount of energy and the outer periphery of the beam circle being the lowest amount of energy. The power setting of the laser 116 will determine the power density, and the size of the patient is taken into account.

In this general approach, there are four basic non overlapping patterns of lasering according to exemplary embodiments of the present invention. Each of the four basic patterns uses a four-point pattern (i.e., four dots outlining a centrally located dot). As a result, the treatments using the laser-based system 100 of FIG. 1 are relatively quick; that is, most treatments are 10-15 minutes in duration.

Figure 12:
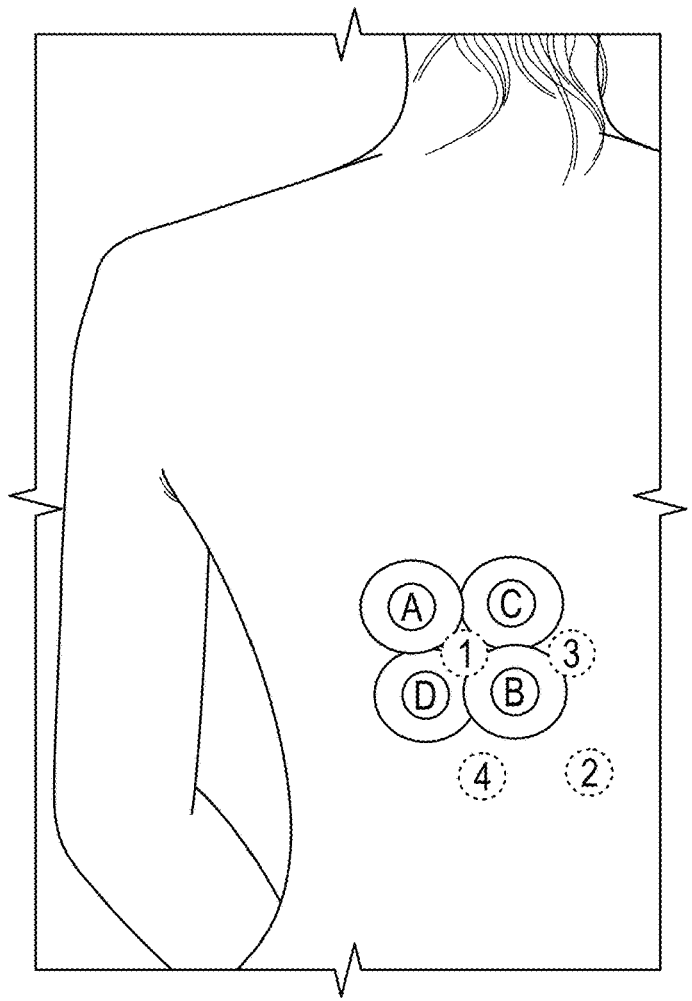
FIGS. 12 and 13 illustrate a back of a human body together with four-point patterns comprising markers to assist a user in locating a laser light beam that is part of the laser-based system of FIG. 1 during treatment of various medical conditions associated with the human back, according to exemplary embodiments of the present invention.

FIG. 12 illustrates the application of four separate four-point patterns of laser light energy to a relatively large area of the human body such as the back as in FIG. 12, thigh, or large arm. This is the simplest and first pattern of the four patterns. Here, the centers of the four applied laser beams do not overlap. However, there is some amount of overlap at the outer periphery of each pattern.

In FIG. 12, the laser 116 is shone onto the skin in a sequential manner. The laser is initially shone onto the area marked 1. After a predefined time, the laser is moved to position 2, which is approximately 5 inches distance from position 1 if the laser is held 10 inches away from the skin. After the predetermined treatment time at position 2, the laser is moved to position 3 and then to position 4. In FIG. 12, each circle marked 1, 2, 3 and 4 is a laser beam center of approximately 0.5 inches in diameter. It is at this beam center where the power density is at the highest. Conversely, the outer circles marked A, B, C and D represent the wider field of about 3.0 inches in diameter out to the outer periphery. By lasering in this manner, the beam centers (1, 2, 3 and 4) of the highest energy density do not overlap whereas the wider fields (A, B, C and D) do overlap to an extent.

Figure 13:
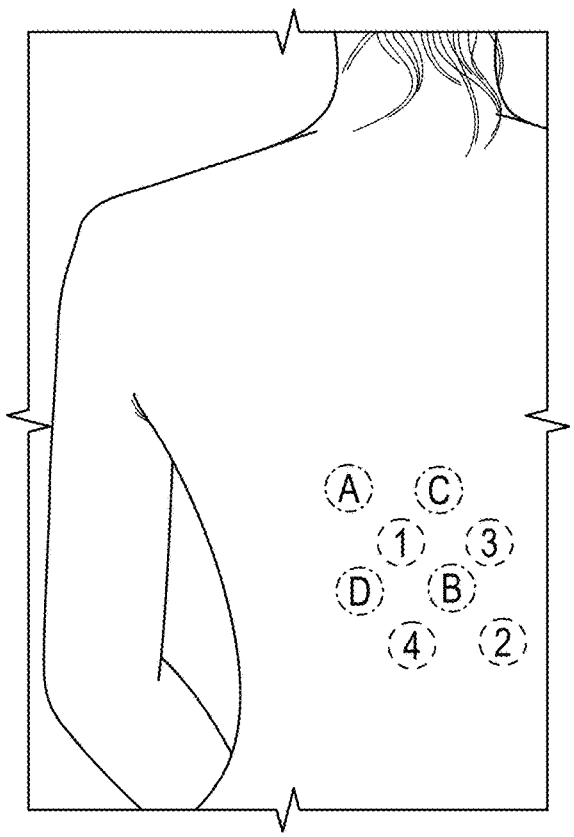

A grid can be marked onto the skin using a white body marker prior to starting the lasering of the skin. A flexible single use grid may be provided for users as a guide for placing the markers on the patient's skin when the laser is held at a distance of 10 inches from the skin. This four-point pattern provides the requisite energy to the area in a most efficient manner. Also, the four-point pattern can be repeated multiple times (e.g., at positions 1, 2, 3 and 4) to treat a larger area, as seen in FIG. 13.

Figure 14:
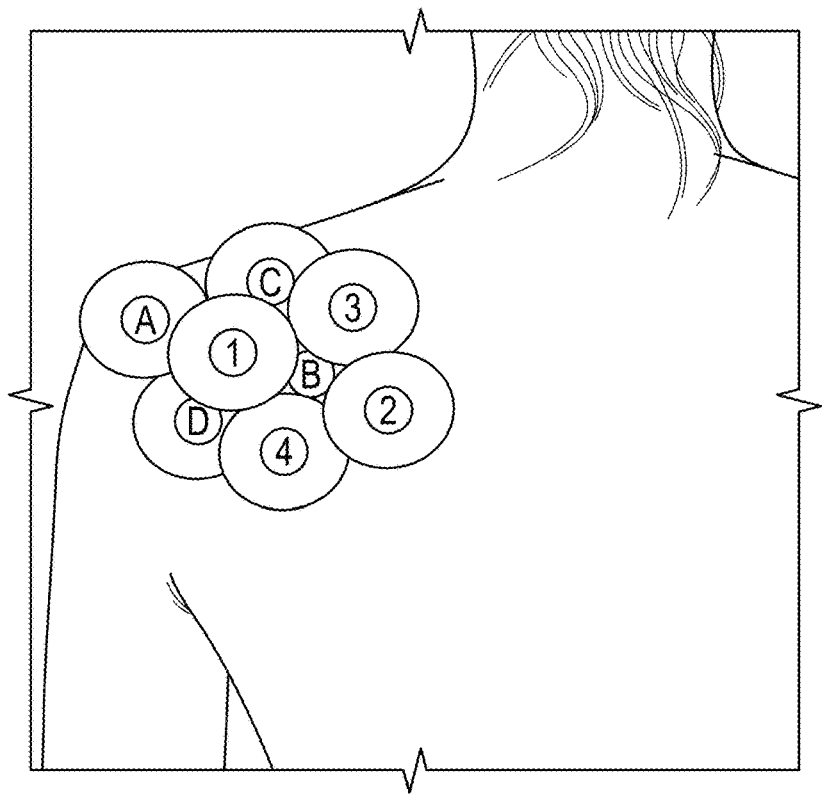
FIG. 14 illustrates the rear portion of a shoulder of a human body together with four-point patterns comprising markers to assist a user in locating a laser light beam that is part of the laser-based system of FIG. 1 during treatment of various medical conditions associated with the shoulder, according to exemplary embodiments of the present invention.

FIG. 14 illustrates the same first four-point pattern as repeatedly applied at positions 1, 2, 3 and 4 to the shoulder. Repeated application of the pattern without overlapping the beam centers will cover the entire injured area of the shoulder, for example, the rotator cuff.

Figure 15:
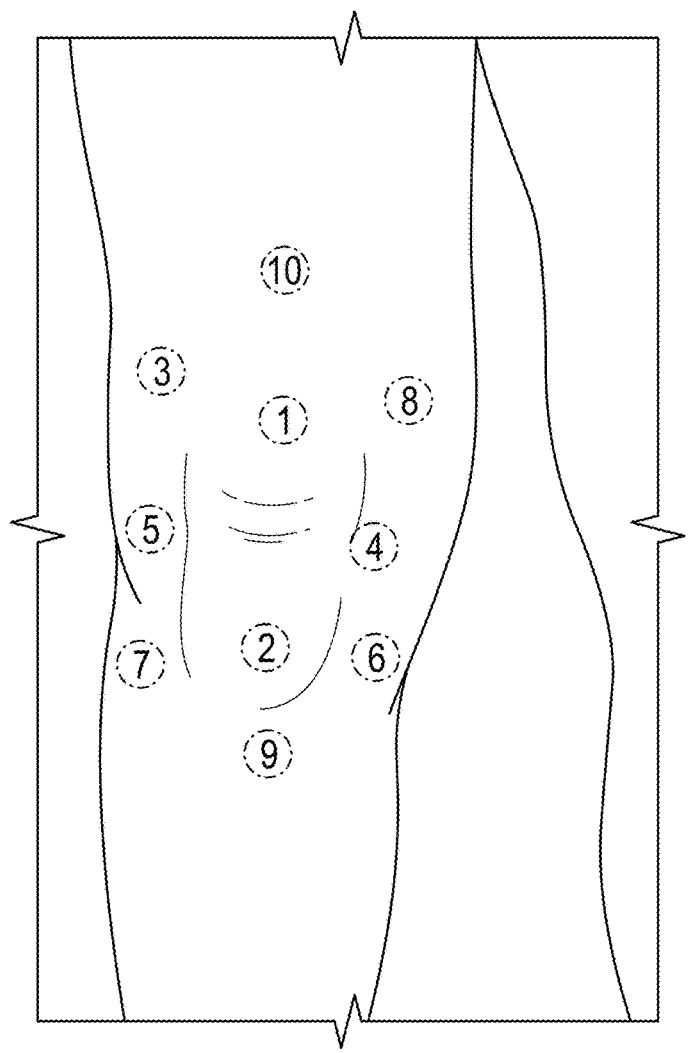
FIG. 15 illustrates the rear portion of a knee of a human body together with various locations comprising markers to assist a user in locating a laser light beam that is part of the laser-based system of FIG. 1 during treatment of various medical conditions associated with the knee, according to exemplary embodiments of the present invention.

FIG. 15 illustrates a knee swollen from injury and the resulting pattern of applied laser light. This is another example of the first four-point pattern. The numbered dots represent each of the corresponding centers of the respective four-point patterns. Again, there is no overlap of the pattern centers.

Although not shown in FIG. 15, a different pattern of laser light energy may be applied to the knee. While having a somewhat odd shape, the same basic four-point pattern can be applied with a broader spacing or distribution between the beam centers. Also, the pattern may be modified or adapted to avoid lasering the center of the kneecap and the patella while only allowing for lasering of the soft tissue around the kneecap. Further, if there is a lot of swelling around the knee, the user can keep utilizing the four-point pattern by either widening the grid size or by adding different grids. The methodology may vary depending upon the physiology of the patient; for example, the grid could be widened for an elderly petite person, whereas multiple grids may be applied for a relatively large athletic knee.

Figure 16:
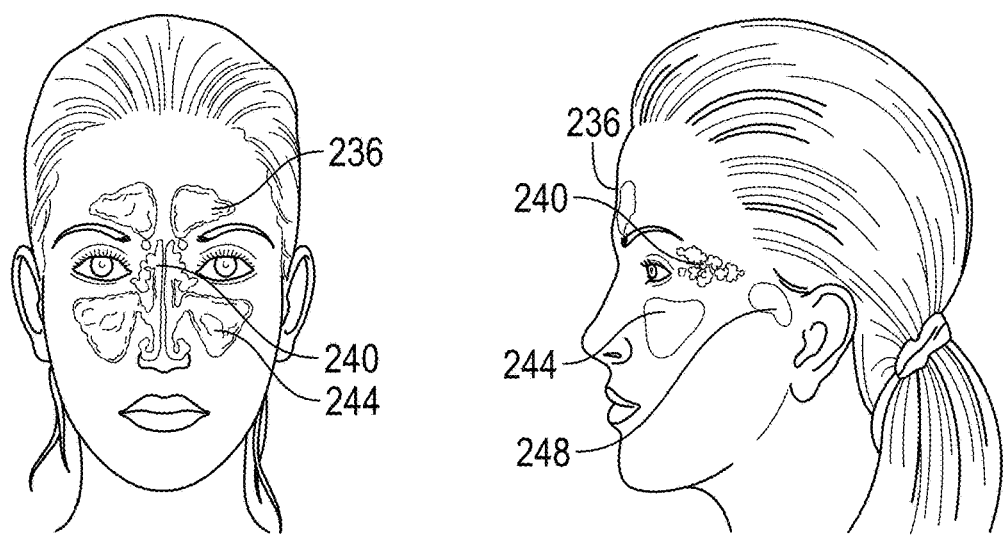
FIGS. 16 and 17 illustrate the face of a human body together with various locations comprising markers to assist a user in locating a laser light beam that is part of the laser-based system of FIG. 1 during treatment of various medical conditions associated with the face, according to exemplary embodiments of the present invention.
Figure 17:
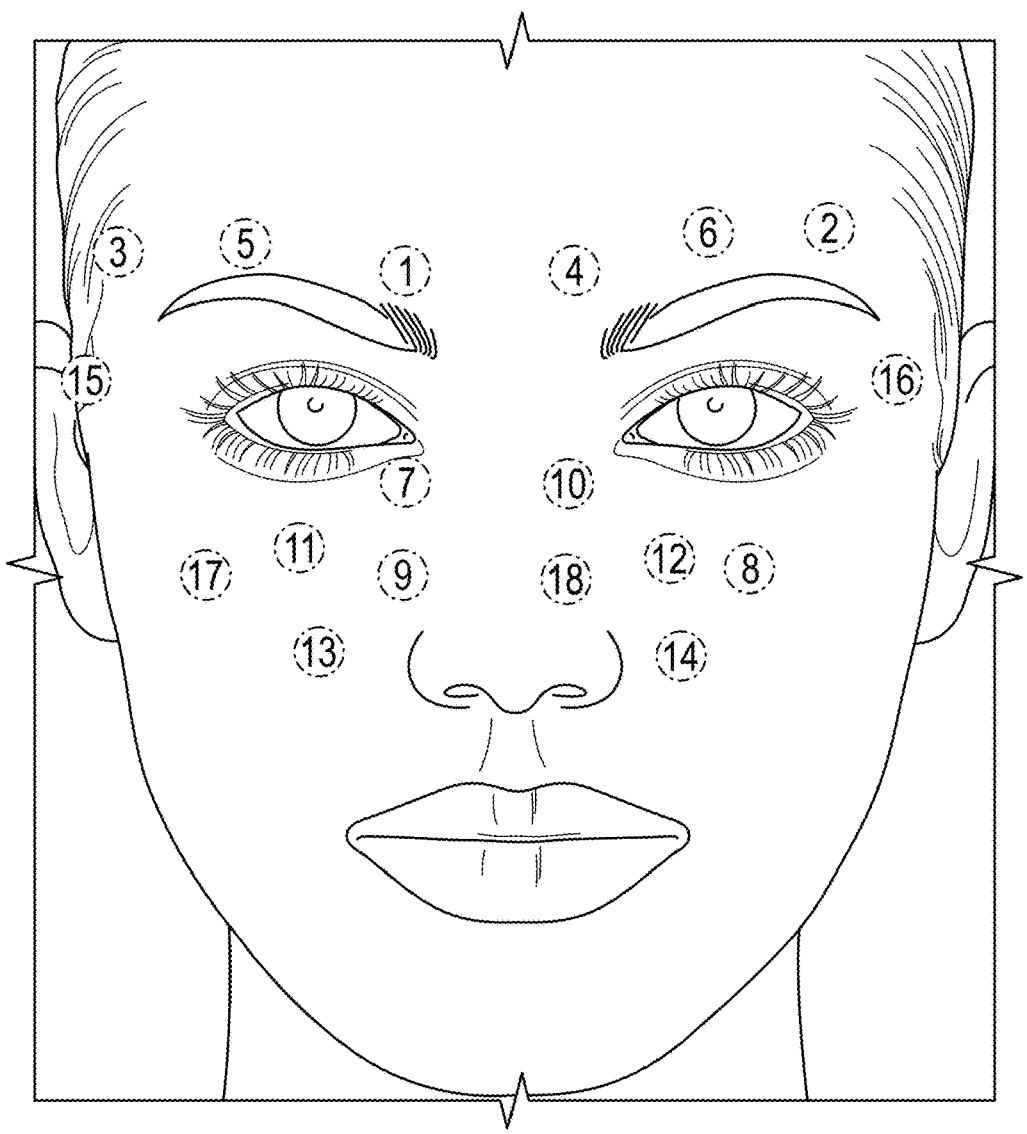

FIGS. 16 and 17 illustrate an exemplary pattern of laser light as applied to sinuses. This may be the second four-point pattern out of the four basic patterns, which is specifically for treatment of the sinuses. As mentioned, the sinuses represent smaller, more discrete areas for treatment as compared to a larger area such as the back. FIG. 16 shows the different areas of the sinuses, while FIG. 17 shows various points each corresponding to the center of the applied laser beam. In FIG. 16, these sinus areas are the frontal sinus area 236, the ethmold sinus area 240, the mallory sinus area 244, and the sphenold sinus area 248. This pattern may be marked onto the patient's face using a laser safe marker prior to commencement of the treatment using the laser 116 to assist a user in properly locating the laser beam. This pattern optimizes efficacy without causing thermal damage.

Figure 18:
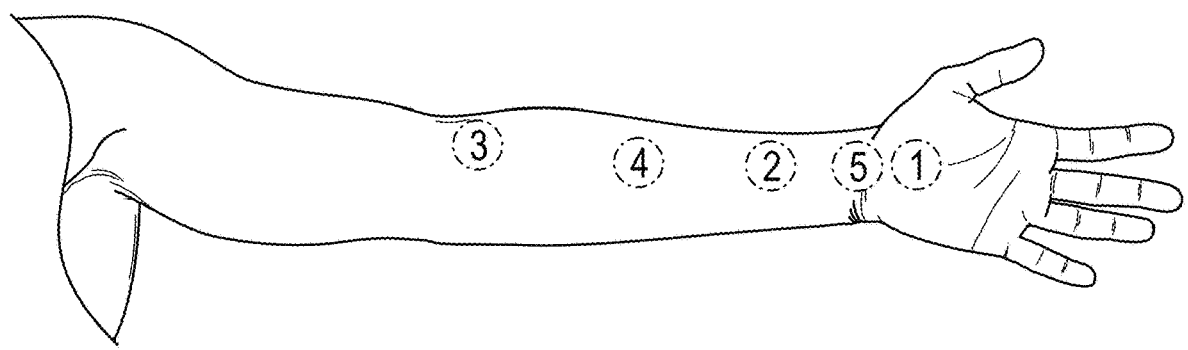
FIG. 18 illustrates the inside of a forearm of a human body together with various locations comprising markers to assist a user in locating a laser light beam that is part of the laser-based system of FIG. 1 during treatment of various medical conditions (e.g., carpal tunnel) associated with the forearm, according to exemplary embodiments of the present invention.

FIG. 18 illustrates an exemplary pattern of laser light applied in a linear manner to an inside portion of a forearm for treatment of, e.g., carpal tunnel. This may be the third four-point pattern out of the four basic patterns. This pattern is specifically for linear treatments of injuries such as, for example, carpal tunnel. For a linear treatment area, the pattern of laser application to the skin is adjusted consistent with the shape of the treatment area. The general principle is to laser the area to be treated and not to overlap the beam centers as the laser 1126 is moved over the tissue.

Figure 20:
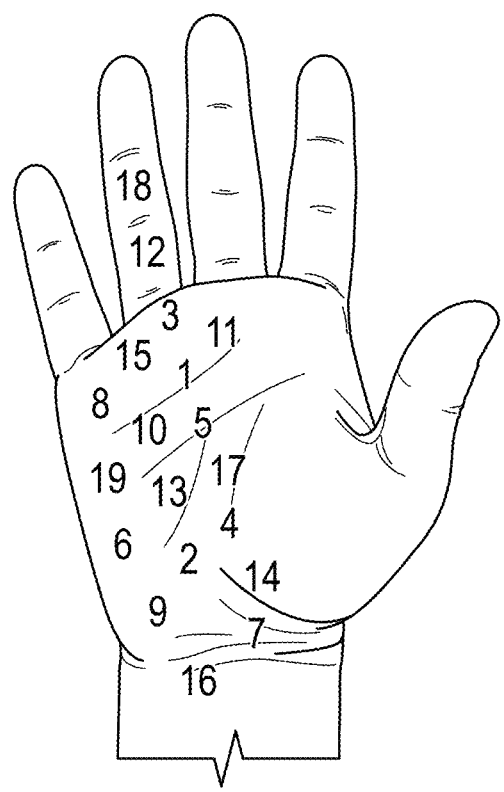
FIGS. 20 and 21 illustrate a human hand having the medical condition of Dupuytren's contracture together with various locations on the hand comprising markers to assist a user in locating a laser light beam that is part of the laser-based system of FIG. 1 during treatment of Dupuytren's contracture, according to exemplary embodiments of the present invention.
Figure 21:
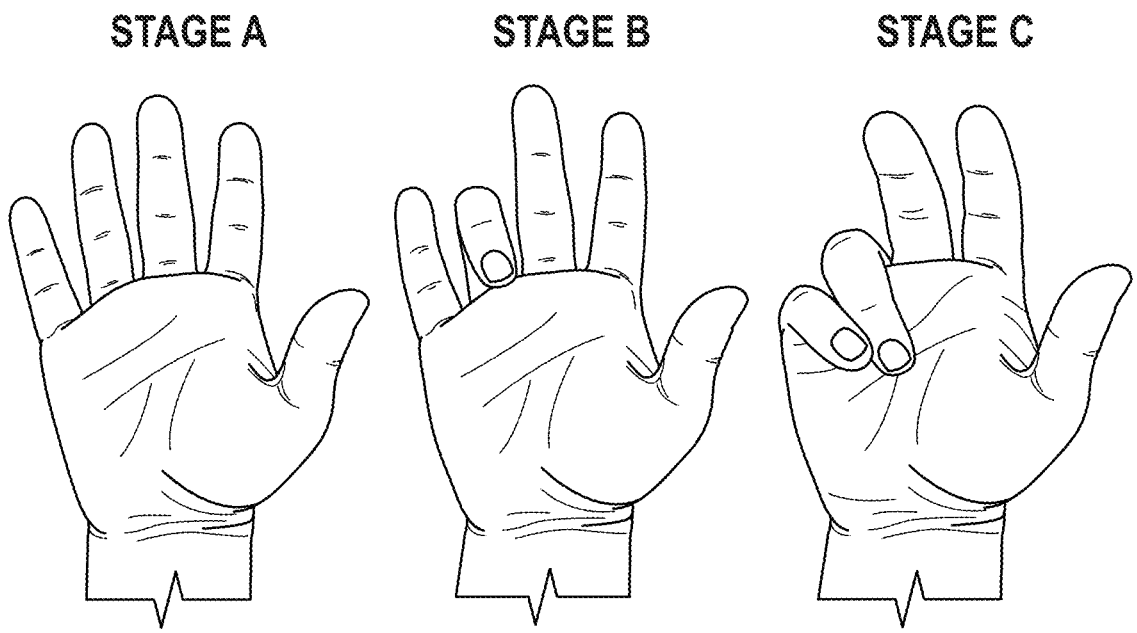

Referring to FIGS. 20 and 21, the fourth pattern out of the four basic patterns is now described and illustrated. Specifically, a method or protocol is described and illustrated for treating a specific medical condition known as Dupuytren's contracture (DC), using the laser-based system 100 of exemplary embodiments of the present invention. The method for treatment to relieve the symptoms of DC is an example of a method used by the laser-based system 100 to relieve fibrosis. DC is a disease of the connective tissues; thus, it can be classified as a rheumatic disease. However, as there are no effective pharmacological interventions and as the treatments are typically surgical and invasive, DC is typically treated as a surgical disease. Peyronies disease, frozen shoulder, and Ledderhose disease are conditions that are typically grouped with DC having a similar etiology, the symptoms of which are similarly relieved by the method of treatment described herein.

DC is typically graded as grades or stages 1 through 4 (or A through D). Stages A through C are illustrated in FIG. 21. The method of treatment of DC with the laser-based system 100 of FIG. 1 is similar and progressive in all grades and stages. According to exemplary embodiments of the present invention, the treatment laser 116 is set to the appropriate power setting in a range of 30 Watts-44 Watts depending upon the skin depth of the patient's hand and the patient's threshold for tolerance of heat. The laser (i.e., the front face 192 of the handpiece 108) is held approximately 6 inches away from the hand such that the laser guide light illuminates a circle of approximately two-inch circumference on the patient's hand. The laser is then held in place for 30-60 seconds depending upon the heat tolerance of the patient. The temperature of the skin in the area on which the laser is shone is a surrogate marker for the dose of energy being delivered to the extracellular matrix of the basal lamina. The skin temperature should increase by at least 10 degrees Celsius. Also, the skin temperature must not increase up to 118 degrees Fahrenheit (approximately 48 degrees Celsius). This delta in skin temperature on the area or spot being lasered should remain for at least 30 seconds. Also, it is not necessary for the laser to remain in place for more than 60 seconds.

The treatment method begins with lasering the palmar side of the hand and forearm as per the numbered sequence illustrated in FIG. 20. In the palm, the focus of the treatment is the nodules and/or the bands. In the forearm, the focus of the treatment is the Flexor carpi ulnaris which is the Motor point that is ⅓rd the distance between the medial epicondyle of humerus and a point on the wrist crease just on the radial side of the flexor carpi ulnaris tendon; the Palmaris Longus which is the Motor Point that is ⅓rd distance between medial epicondyle of humerus and the wrist crease between the flexor carpi radialis and palmaris longus tendon; and the Flexor Carpi Radialis: Motor Point which is 4 inches distal to the middle of the cubital crease.

After lasering point 1 on the hand, the laser is moved to point 2 and so on as the process is repeated at each numbered point or location on the hand. The method or protocol defines a non-overlapping treatment pattern that optimizes laser energy input while minimizing any risk of thermal damage. After the palm and forearm have been fully treated, the dorsal side of the hand is then lasered for 2 minutes using a back-and-forth zig zag pattern in which the laser is continuously moved.

Typically, the treatment described in the method or protocol above is repeated weekly at intervals of 5 to 7 days. There is an initial induction phase where the patient receives the treatment every morning for one week to two weeks. This same induction phase may be utilized for any medical condition that is difficult, and it is advisable for induction to occur in the morning because mitochondria have a circadian rhythm and are much higher energy producers in the morning. Also, for early stages of DC, the condition is usually resolved within 3-5 treatments. Periodic maintenance treatments may be recommended at intervals of 2 to 3 months in order to prevent a recurrence. In DC grades 3 and above, it is generally necessary to complete more than five treatments. Disease classification in DC is evolving which makes it more difficult to provide an accurate correlation of disease stage with time/number of treatments needed to achieve resolution. For the purposes of this protocol and description, the current and most well-established grading system may be used. Ultimately, the grading and number of treatment cycles is at the discretion of the treating clinician and the patient.

In patients in which Grade 4 DC has returned 12-18 months after surgical intervention, treatment with the laser as per the method or protocol described and illustrated herein immediately resolves pain in most patients. Release of the middle finger can be achieved relatively easily through use of the protocol. However, release of the ring and little fingers through laser treatment is less reliable. This may be caused by the fact that post-surgery for DC, there is a relatively large amount of internal residual damage and scar tissue that treatment with the laser may be limited to an extent. The protocol provided herein is a method through stabilization is achieved; i.e., no further progression of the condition post-surgery.

It is advisable that the protocol and method of treatment be practiced in the morning rather than the afternoon or evening. Work in the field of circadian rhythms suggests that mitochondria have a circadian rhythm and are predisposed to increased ATP generation in morning. Observational studies with laser treatment with the methodologies described herein also indicate that a better result, in terms of McGill Pain Scores, range of motion and other symptoms, is achieved if the treatment occurs in the morning.

The protocol and method of treatment described and illustrated herein for Dupuytren's contracture form the base template for the treatment of fibroses in general. For example, a pattern of treatment for frozen shoulder involves setting the laser power to 44 Watts at a distance of 10 inches, the skin temperature delta is 10° C. and the duration of treatment is 60 seconds per laser point. Regardless of body area or disease indication, there should be at least a 10° C. rise in body temperature for at least 45 seconds to ensure reliable efficacy in treatment with the laser-based system 100.

Thus, as seen in the foregoing exemplary patterns, the laser light may be applied in a four-point pattern of non-overlapping beam centers while allowing overlap of the broader areas of laser light. This is done to essentially deliver as much energy as possible to the desired treatment area without causing thermal damage.

Other methods or protocols for treatment of various other medical conditions using the laser-based system 100 of FIG. 1 are described and illustrated herein. These methods of treatment or protocols differ primarily in the power level or irradiance of the applied laser light, as described in detail hereinafter.

Figure 22:
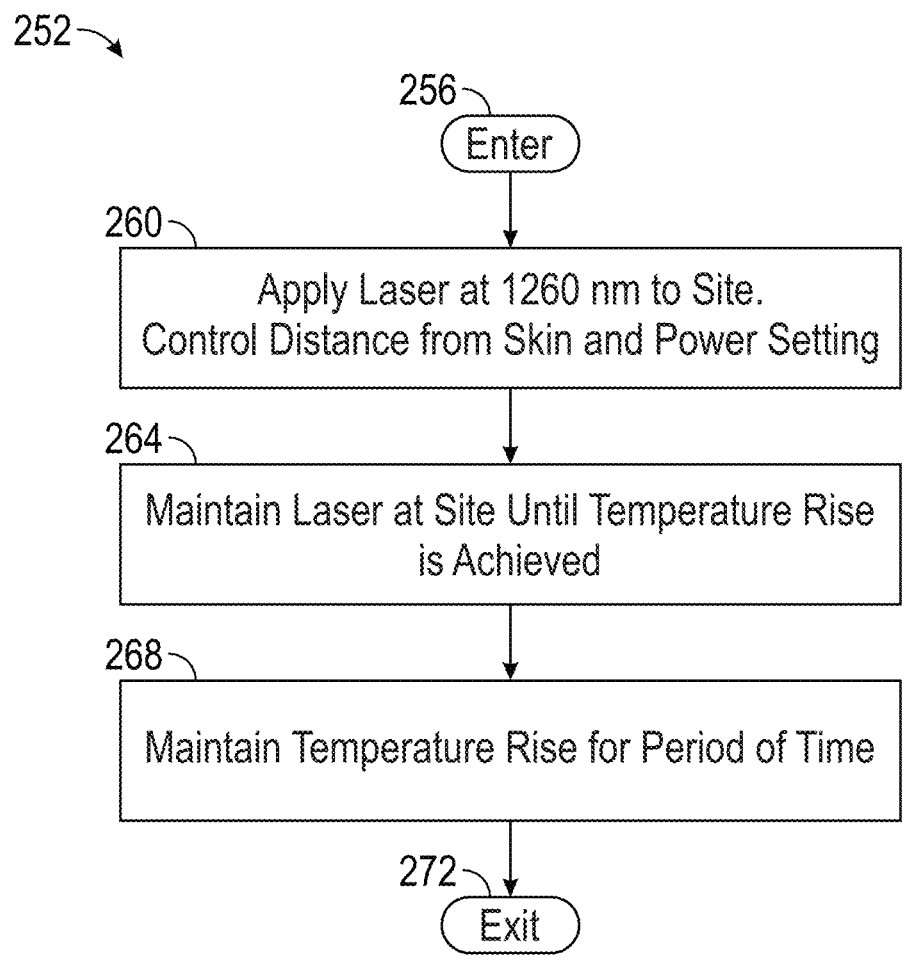
FIG. 22 is a flowchart of steps in a general method for treating various medical conditions in humans or animals using the laser-based system of FIG. 1, according to exemplary embodiments of the present invention.

Referring now to FIG. 22, there illustrated is a flowchart of steps in a method 252 for treating various medical conditions in mammals such as humans and animals using the laser 116. The method 252 of the flowchart of FIG. 22 is described and illustrated herein as a general method for treating the various medical conditions in humans and animals. More specific steps in the method 252, including any variations involving operation of the laser 116 of those steps, are described in greater detail herein, in conjunction with various specific embodiments associated with treatment of certain medical conditions (e.g., cancer).

After an enter step 256 in the method 252, a step 260 is executed in which a person (e.g., a nurse or someone else properly trained in the use of the laser-based system 100 of the present invention) applies the laser 116 to a location on the skin of a patient at a specific location using the handpiece 108. In exemplary embodiments, the laser beam emitted from the laser 116 is applied to the particular site on the skin at a distance up to 10 inches from the skin. However, this distance can vary depending upon the specific treatment method, as described herein.

Also, in accordance with the present invention, the applied laser beam has a wavelength of 1260 nanometers (nm) and a power setting between 2 Watts and 60 Watts. However, this power setting can vary depending upon the specific treatment method, as described herein.

Next, in a step 264, the applied laser beam is maintained at the particular site on the skin until there is a 10 degree Celsius (° C.) rise in temperature at the particular site on the skin. However, this specific temperature rise can vary depending upon the specific treatment method, as described herein.

This is followed by a step 268 in which the 10 degree Celsius temperature rise is maintained at the particular site on the skin for a period of at least 45 seconds and not more than 60 seconds. However, the amount of time that the temperature rise is maintained for can vary depending upon the specific treatment method, as described herein. Nevertheless, maintaining the temperature rise in this manner allows for an irradiance and power density of the applied laser beam of greater than 1.0 Watts per centimeter squared (W/cm$^2$) and less than 2.25 W/cm$^2$ at the particular site on the skin for a period of 45 seconds to 60 seconds. Note, however, that this irradiance and power density, along with the time period, can all vary depending upon the specific treatment method, as described herein.

In exemplary embodiments, steps 260-268 can be repeated each time after the handpiece 108 is moved to another site on the skin of the patient. That is, once a decision is made as to what specific area of the body of the human or animal is to be treated by the laser-based system 100 of embodiments of the present invention, a first location is treated for the requisite time as in steps 260-268. The handpiece 108 is then moved to another location within the overall to be treated with the laser 116, and steps 260-268 are repeated. This process is similar to the locations illustrated in FIGS. 12-18 and FIGS. 20-21. Once the entire area has been treated, the method 252 ends in a step 272.

The methods and protocols described and illustrated herein may be used for ameliorating the symptoms associated with increased longevity or life span. Specifically, peripheral neuralgias, diabetic peripheral paresthesia and wounds relating to diabetes, wound healing from pressure injuries, fibroses, shingles, osteoarthritis, bursitis, tendinitis, joint pain, oral mucositis, acne, psoriasis, dermatitis, burns, edema, etc. Pressure injuries are common and oftentimes impose high healthcare costs and extreme liability exposure for hospitals and other health care facilities such as nursing homes and assisted living.

The methods and protocols may also be used in critical care situations such as cystic fibrosis, hepatic cirrhosis, renal disease, dementia and other acute, chronic and progressive brain disorders, post-operative wound healing, and traumatic brain injuries to name a few. In addition, the methods may be used for improving performance in professional sports people and others engaged in sporting endeavors, enabling them to train harder, longer, and better. In this performance area, the methods may be used to reduce pain and inflammation caused by, e.g., muscle strains and sprains resulting from injuries caused by sports or other activities, and sports conditioning allowing faster recovery and more rapid return to exercise or competition.

Embodiments of the present invention described and illustrated herein provide a number of advantages over the prior art. These advantageous embodiments include the following.

A method for treating a condition in a mammal such as a human or an animal using a laser, the method comprising the steps of applying a laser beam emitted from the laser to a particular site on the skin of the mammal at a distance up to 10 inches from the skin at the particular site, the applied laser beam having a wavelength of 1260 nanometers (nm) and a power setting between 2 Watts and 60 Watts; maintaining the applied laser beam at the particular site on the skin until there is up to a 10-degree Fahrenheit (° F.) increase in temperature at the particular site on the skin; and maintaining the temperature increase of up to 10° F. at the particular site on the skin for a period of at least 45 seconds and not more than 60 seconds, thereby allowing for an irradiance and power density of the applied laser beam of greater than 1.0 Watts per centimeter squared (W/cm$^2$) and less than 2.25 W/cm$^2$ at the particular site on the skin for a period of 45 seconds to 60 seconds.

The previous method wherein the step of applying the laser beam to a particular site on the skin further comprises applying the laser beam to the particular site on the skin that either shows some overt sign of damage or for which there is reasonable belief that it is indicative of some degree of damage to underlying body tissue or bone; and applying the laser beam to a plurality of different spaced apart locations on the skin in the vicinity of the particular site, thereby allowing the applied laser beam to access the stem cell niche immediately proximal to the area of the particular site which provides for energetic activation of the stem cell niche and its contents.

The previous method, wherein the stem cell niche includes a water rich hydrophobic environment, wherein energy from the applied laser beam is absorbed by the water rich hydrophobic environment in the stem cell niche, and wherein by the applied laser beam absorption an energy gradient is created resulting in the mitochondria from the cells directly receiving the laser energy, and/or adjacent cells, are stimulated to emit cytokines resulting in an activation of the stem cell niche and causing the transportation of mitochondrial signals from healthy tissue to unhealthy tissue.

The previous method, wherein the particular site on the skin is in the vicinity of a joint of the mammal, and wherein the step of applying a laser beam emitted from the laser to a particular site on the skin of the mammal comprises applying the laser beam to the particular site at a power setting between 30 Watts and 40 Watts.

The previous method, wherein the joint comprises a knee of the mammal, and wherein the step of applying a laser beam emitted from the laser to a particular site on the skin of the mammal comprises applying the laser beam to a front portion of the knee and a back portion of the knee.

A method for treating cancer in a human or an animal using a laser, including wherein the human or the animal has been administered a checkpoint inhibitor or other modalities of immunotherapy which may be combined with cytotoxic chemotherapy, and wherein the cancer has manifested itself as a solid tumor, the method comprising the steps of applying a laser beam emitted from the laser to a particular site on the skin of the human or the animal at a distance of approximately 10 inches from the skin at the particular site, the particular site on the skin being immediately at, or in the vicinity of the tumor and of the microenvironment field of the tumor, the particular site on the skin also being in the vicinity of local deposits of immune cells, lymph nodes and lymphatic or blood vessels feeding the tumor, and bone marrow, wherein the applied laser beam has a wavelength of 1260 nanometers (nm) and a power setting between 30 Watts and 60 Watts; maintaining the applied laser beam at the particular site on the skin until there is up to a 10 degree Fahrenheit (° F.) increase in temperature at the particular site on the skin; and maintaining the up to 10° F. temperature increase at the particular site on the skin for a period of at least 45 seconds and not more than 60 seconds, thereby allowing for an achievement of an irradiance and power density of the applied laser beam of greater than 1.0 Watts per centimeter squared (W/cm$^2$) and less than 2.25 W/cm$^2$ at the particular site on the skin for a period of 45 seconds to 60 seconds.

The previous method, wherein the step of applying the laser beam comprises applying the laser beam to the particular site at least one day before administration of the checkpoint inhibitor or the other modalities of immunotherapies to thereby activate the stem cell niche of the tumor and its immediate microenvironment.

The previous method, after the step of applying the laser beam to the particular site at least one day before administration of the checkpoint inhibitor or the other modalities of immunotherapies, further comprising the step of applying the laser beam to the particular site during each day of the treatment of the immunotherapy or other chemotherapy either immediately prior to or during administration of therapy.

The previous method, wherein the step of applying the laser beam to the particular site comprises applying the laser beam to a plurality of sites on the skin in the vicinity of the tumor to thereby cover an area of the tumor and its immediate microenvironment.

The previous method, wherein the method further comprises a method for stimulating microsatellite instability ("MSI") or other mechanisms which increase the immunogenicity of the tumor to the endogenous immune system likely as a result of the production of the tumor associated neo-antigens which renders the tumor more susceptible to tumor directed immunotherapies and thereby correlates with sensitivity to the other modalities of immunotherapy aimed at both the tumor cells and its microenvironment.

The previous method, wherein the method further comprises a method for stimulating the cGAS/STING innate immune pathway by inducing intracellular production of small endogenous nucleic acids, wherein the STING activation stimulates cytokine/chemokine production and hence infiltration of therapeutic immune effector cells.

The previous method, wherein the method further comprises a method for stimulating the function of exhausted T-Cell tumor infiltrates which are no longer functional and are no longer susceptible to re-activation by various stimuli.

The previous method, wherein the method further comprises a method for altering tumor microvesicle ("MV") production, function, loading and release from the tumor, thereby altering the dissemination of soluble molecules which have been shown to prepare the distant metastatic niche for seeding by metastatic tumor cells.

A method for treating an ear of a human or an animal using a laser, the method comprising the steps of: applying a laser beam emitted from the laser to a particular site on the skin of the human or the animal, the particular site being an ear of the human or the animal or an area of the skull in the vicinity of the ear of the human or the animal, wherein the laser beam is applied at a distance of approximately 2 inches to 3 inches from the skin at the particular site, wherein the applied laser beam has a wavelength of 1260 nanometers (nm) and a power setting between 2 Watts and 10 Watts; maintaining the applied laser beam at the particular site on the skin until a temperature increase of at least 5 degrees Fahrenheit (° F.) is achieved at the particular site on the skin; and maintaining the at least 5° F. temperature increase at the particular site on the skin for a period of at least 20 seconds, thereby allowing for an achievement of an irradiance and power density of the applied laser beam of 1.0 Watts per centimeter squared (W/cm$^2$) at the particular site on the skin for a period of 45 seconds to 60 seconds.

The previous method, wherein the step of applying the laser beam to a particular site on the skin further comprises applying the laser beam to up to three different spaced apart locations on the skin in the vicinity of an ear canal of the ear and down to a base of an ear lobe of the ear.

A method for treating a condition in a mammal such as a human or an animal using a laser, the method comprising the steps of applying a laser beam emitted from the laser to a particular site on the skin of the mammal, the particular site being a scalp or a forehead of the human or the animal, wherein the laser beam is applied at a distance of up to 3 inches from the skin at the particular site, wherein the applied laser beam has a wavelength of 1260 nanometers (nm) and a power setting between 10 Watts and 20 Watts; maintaining the applied laser beam at the particular site on the skin until there is a 5 degree Fahrenheit (° F.) increase in temperature at the particular site on the skin; and maintaining the 5° F. temperature increase at the particular site on the skin for a period of at least 20 seconds and not more than 40 seconds, thereby allowing for an achievement of an irradiance and power density of the applied laser beam of greater than 1.0 Watts per centimeter squared (W/cm$^2$) at the particular site on the skin for a period of 20 seconds to 40 seconds, and thereby allowing for energy from the applied laser beam to pass into tissue of a brain or central nervous system or peripheral nervous system of the human or the animal which results in an increase in vascular permeability and allows the energy from the applied laser beam to access the one or more stem cell niches in the superficial aspects of the brain, central and peripheral nervous systems, thereby creating a positive energy gradient therein.

In addition, a method for activating the stem cell niche, providing for stem cell activation and the sustained initiation of a cascade of intracellular activities focused on decreasing an inflammatory response and resulting in the restoration of normal cellular function. This inflammatory response that is modulated may be e.g., reduced in the situation of an inappropriate pro inflammatory response resulting in oedema, and/or in slow to heal wounds, and/or fibrosis. Alternatively, it may instead be an inappropriate anti-inflammatory response resulting in an inadequate response from the immune system for example, infection, and it may also be an inflammatory response that results in the prolonged activation of pain receptors in which case the intracellular cascade has an effect upon afferent neurons.

A method for activating the stem cell niche, providing for stem cell activation and the sustained initiation of a cascade of intracellular activities resulting in the stimulation of T cell subsets necessary or useful for reducing and/or eliminating neoplasms and oncological conditions.

A method for activating the stem cell niche, providing for stem cell activation and the sustained initiation of a cascade of intracellular activities focused on decreasing a negative inflammatory response and resulting in the stimulation of T cell subsets to break tolerance associated with neoplasms and oncological conditions.

A method for delaying inflammatory joint degradation and potentiating the effectiveness of pre-surgery interventions including but not limited to corticosteroid injections, by activating the stem cell niche, by providing for stem cell activation and the sustained initiation of a cascade of intracellular activities focused on decreasing an inflammatory response and resulting in the restoration of normal cellular function.

A method for non-invasively accessing and modulating meridians and pressure points used in Traditional Chinese Medicine.

A method for increasing blood circulation to the central nervous system including the brain, and the associated stem cell niches held therein, initiating and sustaining a cascade of intracellular activities the effects of which restore the normal functioning of immune system components including the glymphatic system resulting in effects including but not limited to the removal of scar tissue components including amyloid from the CNS (including brain), leading to an improvement in cognitive function and reduction in the signs symptoms associated with various neurodegenerative conditions including but not limited to Alzheimers, Parkinson's, and Lewy Body dementia.

A method for activating the stem cell niche in the central nervous system including the brain and associated stem cell niches held therein, initiating and sustaining a cascade of intracellular activities the effects of which restore the normal functioning of immune system components including the activation and stimulation of the glymphatic system resulting in effects including but not limited to the removal of scar tissue components including amyloid from the CNS (including brain), leading to an improvement in cognitive function and reduction in the signs symptoms associated with various neurological and neurodegenerative conditions including but not limited to CTE (chronic traumatic encephalopathy) and TBI (traumatic brain injury), Alzheimers, Parkinson's, and Lewy Body dementia.

A method for increasing blood circulation to the central nervous system including the brain, and the associated stem cell niches held therein, initiating and sustaining a cascade of intracellular activities the effects of which restore the normal functioning of immune system components including but not limited to the glymphatic system resulting in effects including but not limited to the removal of scar tissue components including amyloid from the CNS (including brain), leading to an improvement in cognitive function and reduction in the symptoms associated with traumatic brain injury.

A method for activating the stem cell niche in the central nervous system including the brain and associated stem cell niches held therein, initiating and sustaining a cascade of intracellular activities the effects of which restore the normal functioning of immune system components including but not limited to the glymphatic system resulting in effects including but not limited to the removal of scar tissue components including e.g., amyloid from the CNS (including brain), leading to an improvement in cognitive function and reduction in the signs symptoms associated with traumatic brain injury.

A method for turning "cold" tumors to "hot" and therefore allowing cell-based or checkpoint-based immunotherapies to work/synergize with laser Rx. Specifically, by stimulating the release of pro inflammatory chemokines and cytokines in the tumor which stimulate the migrations and infiltration of effector T cells and other effector cells into the tumor for Rx benefit.

A method for modifying the structure and functions of the tumor microenvironment (TME) by increasing permeability to effector Rx cells and cancer therapeutics. Specifically, by altering neo angiogenesis, vasculogenesis and tumor lymphatic function, and other aspects of tumor biology.

A method for altering the structure function density of the tumor extracellular matrix (ECM) such that tumor Rx is stimulated by either therapeutic cells or drugs.

A method for increasing the neo-antigen load in tumors which correlates with response to immune therapies. The neo antigens could be nucleic acid, protein, or lipid based.

A method for stimulating DNA repair and microsatellite instability (MSI) within the tumor which correlates with Rx sensitivity in many solid tumors.

A method for stimulating the cGAS/STING innate immune pathway by inducing the intracellular production of small endogenous nucleic acids. STING activation serves to stimulate cytokine/chemokine production and hence infiltration of therapeutic immune effector cells.

A method for stimulating the function of exhausted T-Cell tumor infiltrates which are no longer functional and are no longer susceptible to re-activation by various stimuli.

A method for altering the function, recruitment and intra tumoral dynamics of cancer stem cells and their ability to be "seen" by both tumor specific immune effector cells and therapeutics which are designed to target cancer stem cells.

A method for altering tumor microvesicle (MV) production, function, loading and release from a tumor thereby altering the dissemination of soluble molecules which have been shown to prepare the distant metastatic niche for seeding by metastatic tumor cells.

A method for altering cell-cell and cell-ECM interactions which stimulate cell migration from the tumor and all subsequent steps in micro metastasis formation: intravasation, systemic delivery, and extravasation in a distant organ.

Figure 23:
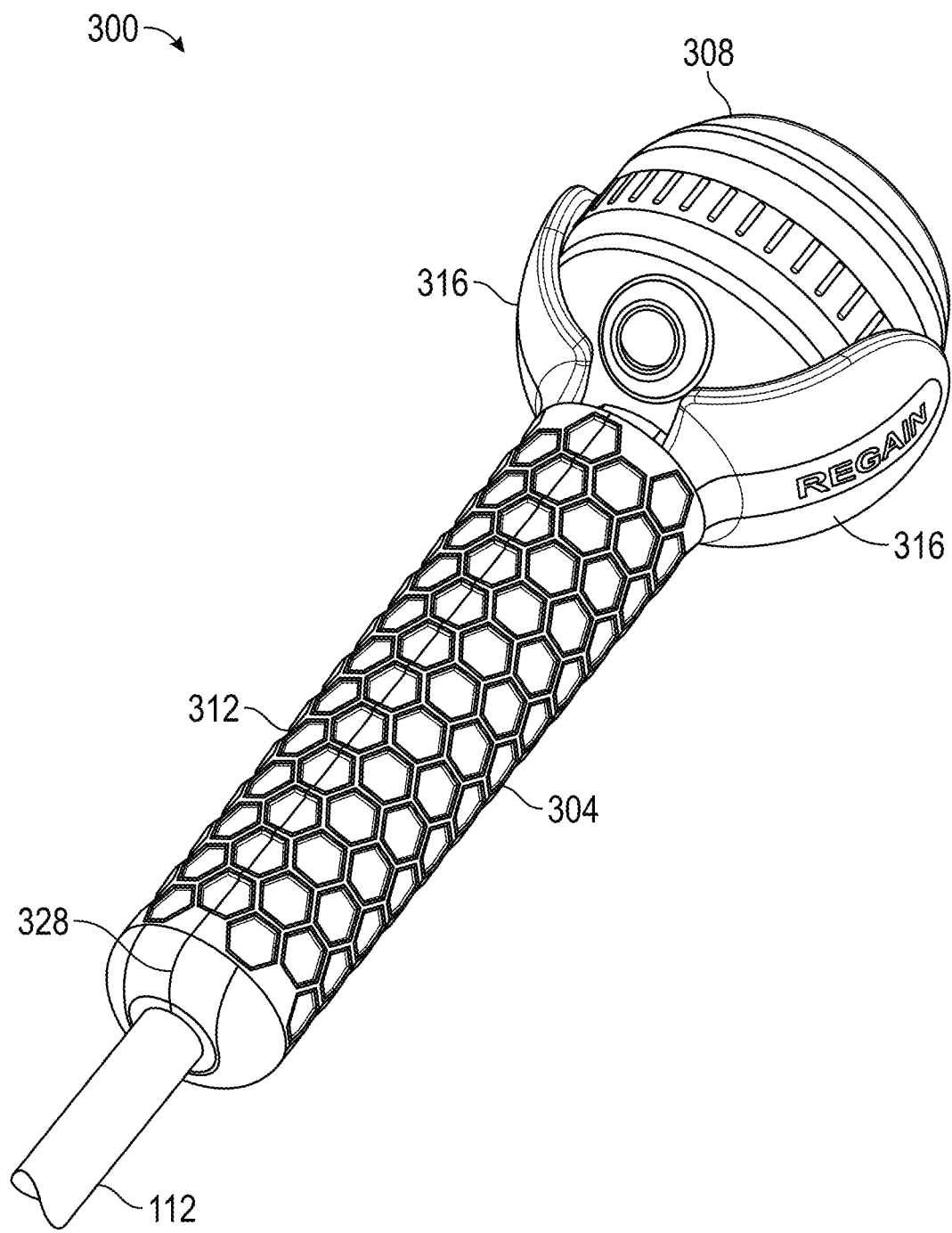
FIG. 23 is a perspective view of an alternative embodiment of the handpiece of the laser-based system of FIG. 1.
Figure 24:
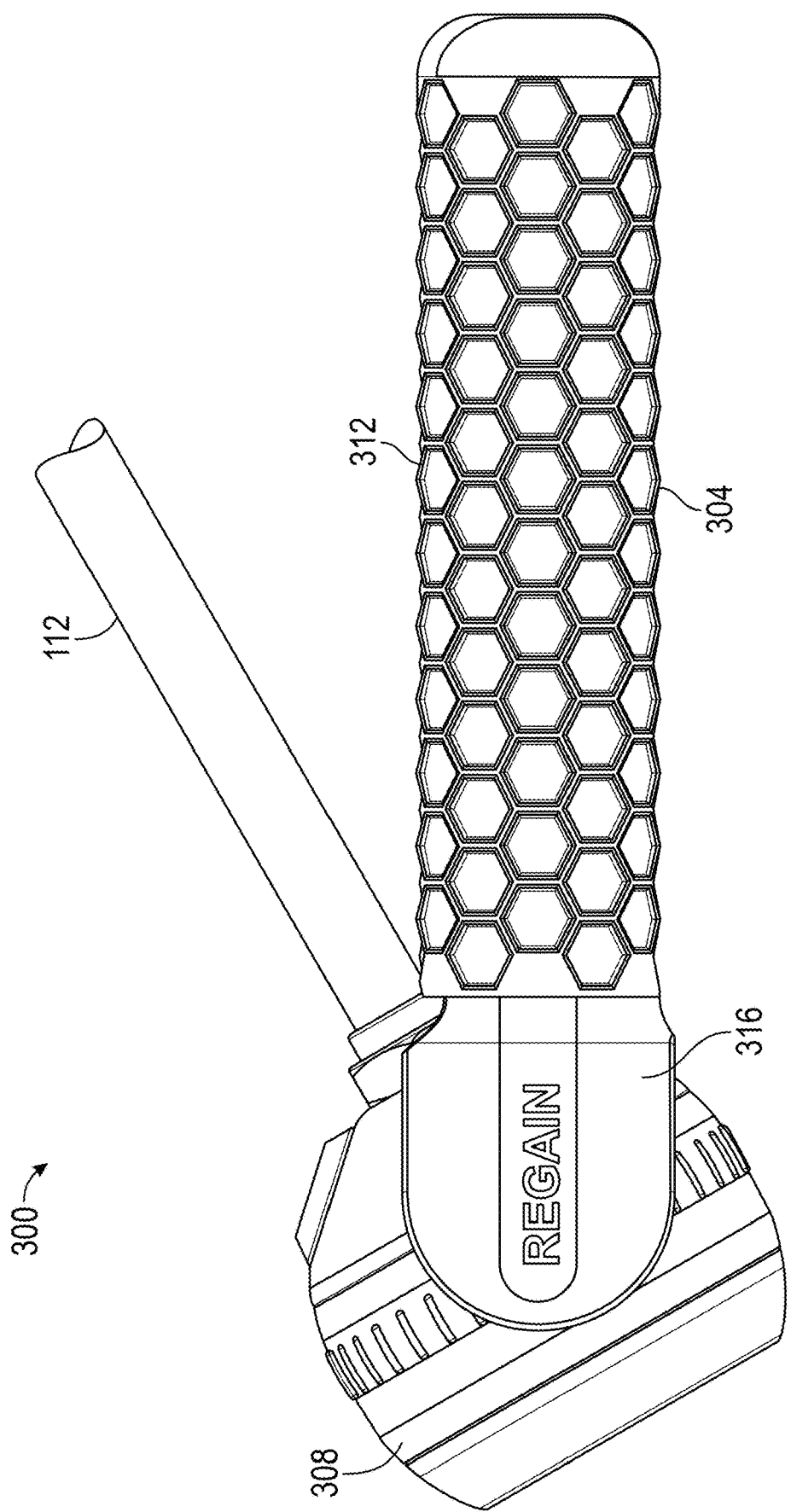
FIG. 24 is a side view of the handpiece of FIG. 23 showing a handle portion of the handpiece moved into a predetermined angular position with respect to a sphere portion of the handpiece, according to exemplary embodiments of the present invention.
Figure 25:
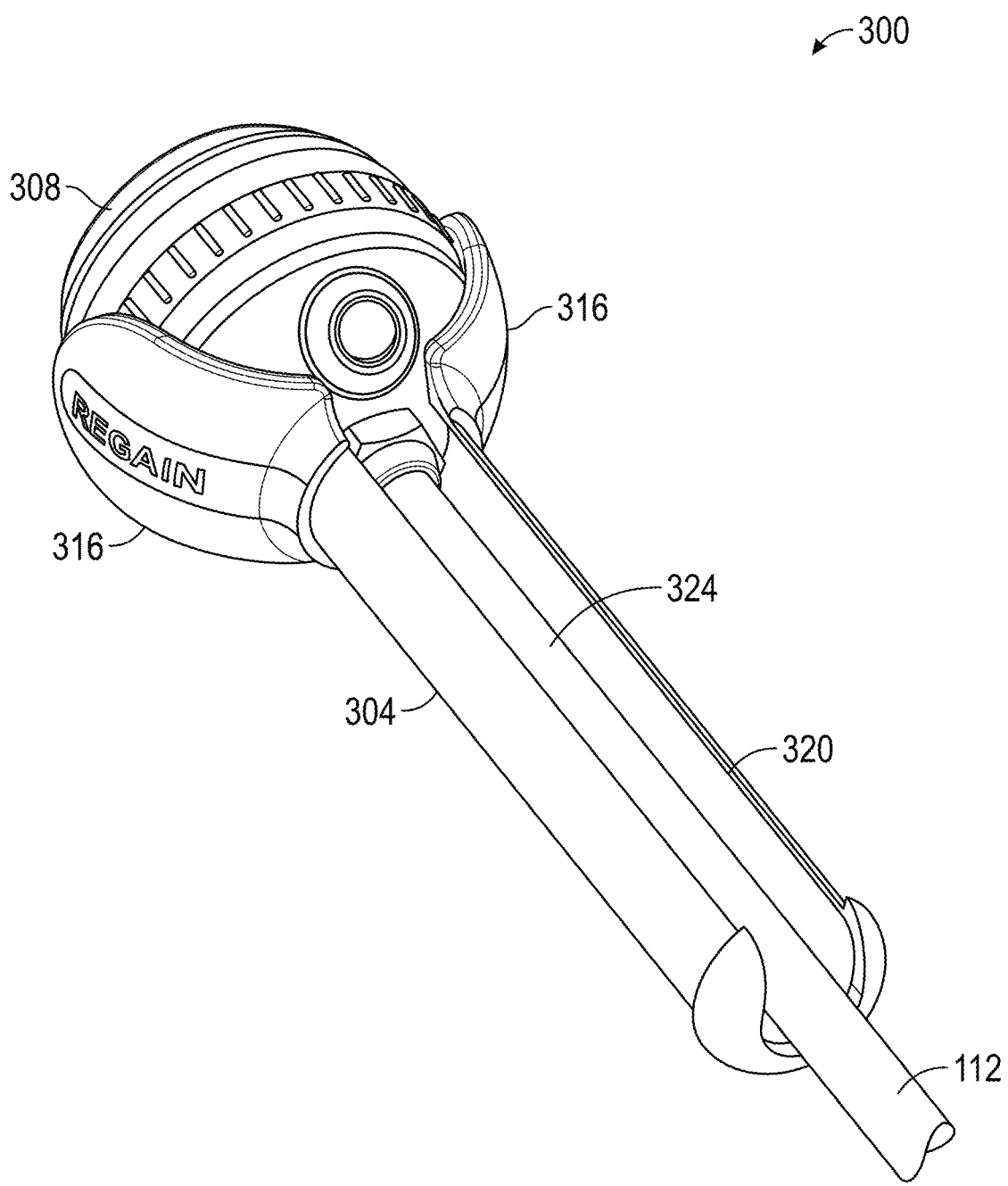
FIG. 25 is a top perspective view of the handpiece of FIG. 23 showing the handle portion of the handpiece without the outer covering, according to exemplary embodiments of the present invention.

Referring now to FIGS. 23-25, there illustrated are various views of an alternative embodiment of a handpiece 300 that is part of the laser-based system 100 of FIG. 1. The handpiece 300 is similar in many respects to the handpiece 108 of the exemplary embodiments of the laser-based system 100 of FIGS. 1-9 described in detail hereinabove. Specifically, FIG. 23 is a perspective view of the handpiece 300. FIG. 24 is a side view of the handpiece 300 that shows a handle portion 304 of the handpiece 300 moved into a predetermined angular position (e.g., 30 degrees) with respect to a sphere portion 308 of the handpiece 300. FIG. 25 is a top perspective view of the handpiece 300 showing the handle 304 without an outer covering 312.

The sphere 308 comprises the main body portion of the handpiece 300 and houses most of the handpiece components described and illustrated hereinabove. The handle 304 allows the cable 112 to sit within and along the length of the handle 304. One end of the cable 112 connects within the sphere 308, while the other end of the cable 112 connects inside the box 104 (FIG. 1). In this alternative embodiment of the handpiece 300, the handle 304 is rotatably affixed to the sphere 308 through use of two diametrically opposed prongs 316 located at the sphere end of the handle 304. The rotatable connection of the prongs 316 to the sphere 308 allows the handle 304 to pivot or rotate with respect to the sphere 308: specifically with respect to an axis passing through the sphere 308 and perpendicular to the flat front face 192 of the sphere 308. This rotatable adjustment feature of the handle 300 allows the user to rotate the handpiece 300 to a desired angle with respect to the sphere. This allows the handpiece 300 to be relatively more easy and less fatiguing to use over the typical period of time that the laser-based system 100 is in use to treat a human or an animal.

In exemplary embodiments, the handle 304 may be rotated in 30-degree increments by the user of the handpiece 300; that is to angles of 30 degrees, 60 degrees and 90 degrees—all with respect to the sphere 308. However, it should be understood that these angles of rotation are purely exemplary. Any amount of angular rotation may be utilized by one of ordinary skill in the art in light of the teachings herein.

In exemplary embodiments, both the handle 304 and the sphere 308 may comprise a rugged plastic material. The handle outer covering 312 may comprise rubber or other material that promotes non-slip gripping of the handpiece 300 by the user. The outer covering 312 may have a honeycomb or other pattern formed therein to promote such non-slip gripping.

As best seen in FIG. 25 with the outer covering 312 removed, an underlying plastic portion 320 of the handle 304 has a slot or groove 324 formed therein. The slot 324 is wide enough to allow the cable 112 to pass through and out of the handle 304 when the user desires to angle the handle 304 with respect to the sphere 308. Specifically, the outer covering 312 is not contiguous but instead has a seam 328 that is placed over the slot 324. When the handle 304 is then rotated to an angle, the cable 112 passes through the slot 324 and the seam 328. The seam 328 is designed to ensure that the user holding the handle 304 experiences a seamless surface of the outer covering 312 without any noticeable cutout. When a user adjusts the angle of the handle 304, the cable 112 moves through the slot 324 and outside of the handle 304 (FIG. 24), thereby enabling the sphere 308 to rotate freely while the user maintains a secure grip on the handle 304.

The terminology used herein is for the purpose of describing particular embodiments of the invention only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the invention is provided in detail in connection with only a limited number of embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Additionally, while various embodiments of the invention have been described, it is to be understood that the exemplary embodiments may include only some of the described exemplary aspects. Accordingly, the invention is not to be seen as limited by the foregoing description but is only limited by the scope of the appended claim.

The invention claimed is:

1. A method for treating a condition in a human or an animal using a laser, the method comprising the steps of:
    applying a laser beam emitted from the laser to a particular site on the skin of the human or the animal at a distance up to 10 inches from the skin at the particular site, the applied laser beam having a wavelength of 1260 nanometers (nm) and a power setting between 2 Watts and 60 Watts;
    maintaining the applied laser beam at the particular site on the skin until there is up to a 10-degree Fahrenheit (° F.) increase in temperature at the particular site on the skin;
    maintaining the temperature increase of up to 10° F. at the particular site on the skin for a period of at least 45 seconds and not more than 60 seconds, thereby allowing for an irradiance and power density of the applied laser beam of greater than 1.0 Watts per centimeter squared ($W/cm^2$) and less than 2.25 $W/cm^2$ at the particular site on the skin for a period of 45 seconds to 60 seconds
    wherein the step of applying the laser beam to a particular site on the skin further comprises:
        applying the laser beam to the particular site on the skin that either shows some overt sign of damage or for which there is reasonable belief that it is indicative of some degree of damage to underlying body tissue or bone; and
        applying the laser beam to a plurality of different spaced apart locations on the skin in the vicinity of the particular site, thereby allowing the applied laser beam to access the stem cell niche immediately proximal to the area of the particular site which provides for energetic activation of the stem cell niche and its contents;

wherein the particular site on the skin is in the vicinity of a joint of the human or the animal, and wherein the step of applying a laser beam emitted from the laser to a particular site on the skin of the human or the animal comprises applying the laser beam to the particular site at a power setting between 30 Watts and 40 Watts; and wherein the joint comprises a knee of the human or the animal, and wherein the step of applying a laser beam emitted from the laser to a particular site on the skin of the human or the animal comprises applying the laser beam to a front portion of the knee and a back portion of the knee.

2. The method of claim 1, wherein the stem cell niche includes a water rich hydrophobic environment, wherein energy from the applied laser beam is absorbed by the water rich hydrophobic environment in the stem cell niche, and wherein by the applied laser beam absorption an energy gradient is created resulting in the mitochondria from the cells directly receiving the laser energy, and/or adjacent cells, are stimulated to emit cytokines resulting in an activation of the stem cell niche and causing the transportation of mitochondrial signals from healthy tissue to unhealthy tissue.

* * * * *